US012029565B2

(12) United States Patent
Block et al.

(10) Patent No.: US 12,029,565 B2
(45) Date of Patent: *Jul. 9, 2024

(54) SYSTEMS AND METHODS FOR NERVE MAPPING AND MONITORING

(71) Applicant: SidewayStrategies LLC, Walnut Creek, CA (US)

(72) Inventors: Jonathan D. Block, Walnut Creek, CA (US); Hieu T. Ball, Walnut Creek, CA (US)

(73) Assignee: SidewayStrategies LLC, Walnut Creek, CA (US)

( * ) Notice: Subject to any disclaimer, the term of this patent is extended or adjusted under 35 U.S.C. 154(b) by 417 days.

This patent is subject to a terminal disclaimer.

(21) Appl. No.: 17/223,332

(22) Filed: Apr. 6, 2021

(65) Prior Publication Data

US 2021/0361212 A1 Nov. 25, 2021

Related U.S. Application Data

(63) Continuation of application No. 16/025,249, filed on Jul. 2, 2018, now Pat. No. 10,973,451, which is a
(Continued)

(51) Int. Cl.
*A61B 5/24* (2021.01)
*A61B 1/32* (2006.01)
(Continued)

(52) U.S. Cl.
CPC ............... *A61B 5/24* (2021.01); *A61B 1/32* (2013.01); *A61B 5/4029* (2013.01);
(Continued)

(58) Field of Classification Search
CPC ............ A61B 5/04001; A61B 5/04012; A61B 5/0478; A61B 5/0484; A61B 5/0488;
(Continued)

(56) References Cited

U.S. PATENT DOCUMENTS 7,231,256 B2 6/2007 Wahlstrand et al.
7,522,953 B2 4/2009 Kaula et al.
(Continued)

FOREIGN PATENT DOCUMENTS

EP 2289448 3/2011
WO WO 2014/063163 4/2014
WO WO 2018/014007 1/2018

OTHER PUBLICATIONS

Bernard et al., "Electrical Performances of a New Multipolar Micro-Stimulator"; 10th Annual Conference of the International FES Society, Montreal Canada, Jul. 2005; 3 pages.
(Continued)

*Primary Examiner* — Patrick Fernandes
(74) *Attorney, Agent, or Firm* — Knobbe, Martens, Olson & Bear, LLP

(57) ABSTRACT

Embodiments can include a nerve mapping and monitoring system that can include a multi-polar stimulation unit, an electrical connector, an instrument having a grid array, where the grid array can comprise a plurality of electrodes, where each of the plurality of electrodes can be configured to be stimulated by the multi-polar stimulation unit, a recording element, where the recording element can be configured to detect a muscle response elicited by the grid array, and a computer, where the computer can be configured to monitor the muscle response elicited by the grid array such that neural structures can be identified and avoided.

20 Claims, 17 Drawing Sheets

Related U.S. Application Data continuation of application No. 14/059,256, filed on Oct. 21, 2013, now Pat. No. 10,016,142.

(60) Provisional application No. 61/715,956, filed on Oct. 19, 2012.

(51) Int. Cl.
   *A61B 5/00* (2006.01)
   *A61B 5/296* (2021.01)
   *A61M 29/00* (2006.01)

(52) U.S. Cl.
   CPC ............ *A61B 5/6847* (2013.01); *A61B 5/742* (2013.01); *A61M 29/00* (2013.01); *A61B 5/296* (2021.01)

(58) Field of Classification Search
   CPC ..... A61B 5/0492; A61B 5/6847; A61B 5/742; A61B 5/743; A61B 1/32; A61B 5/4029; A61B 5/24; A61B 5/296; A61M 29/00
   See application file for complete search history.

(56) References Cited

U.S. PATENT DOCUMENTS

| | | |
|---|---|---|
| 7,959,577 B2 | 6/2011 | Schmitz et al. |
| 7,962,191 B2 | 6/2011 | Marino et al. |
| 8,005,535 B2 | 8/2011 | Gharib et al. |
| 8,137,284 B2 | 3/2012 | Miles et al. |
| 8,165,653 B2 | 4/2012 | Marino et al. |
| 8,172,750 B2 | 5/2012 | Miles et al. |
| 8,206,312 B2 | 6/2012 | Farquhar |
| 8,224,453 B2 | 7/2012 | De Ridder |
| 8,644,903 B1 | 2/2014 | Osa et al. |
| 8,660,657 B2 | 2/2014 | Saoji |
| 8,914,121 B2 | 12/2014 | Moffitt et al. |
| 8,942,801 B2 | 1/2015 | Miles et al. |
| 9,248,279 B2 | 2/2016 | Chen et al. |
| 10,016,142 B2 | 7/2018 | Block et al. |
| 10,973,451 B2 | 4/2021 | Block et al. |
| 2005/0182456 A1 | 8/2005 | Ziobro et al. |
| 2006/0161235 A1 | 7/2006 | King |
| 2006/0276853 A1 | 12/2006 | Tass et al. |
| 2008/0167574 A1 | 7/2008 | Farquhar |
| 2009/0177112 A1 | 7/2009 | Gharib et al. |
| 2010/0268298 A1 | 10/2010 | Moffitt et al. |
| 2011/0082383 A1 | 4/2011 | Cory et al. |
| 2011/0230785 A1 | 9/2011 | Higgins et al. |
| 2011/0269172 A1 | 11/2011 | Eberle et al. |
| 2012/0095360 A1 | 4/2012 | Runney et al. |
| 2013/0035741 A1 | 2/2013 | Kolen et al. |
| 2013/0131743 A1 | 5/2013 | Yamasaki et al. |
| 2014/0057232 A1 | 2/2014 | Wetmore et al. |
| 2014/0378941 A1 | 12/2014 | Su et al. |
| 2015/0005680 A1 | 1/2015 | Lipani |
| 2015/0012067 A1 | 1/2015 | Bradley et al. |
| 2015/0012068 A1 | 1/2015 | Bradley et al. |
| 2015/0032022 A1 | 1/2015 | Stone et al. |
| 2015/0057722 A1 | 2/2015 | Faltys et al. |
| 2015/0066104 A1 | 3/2015 | Wingeler et al. |
| 2015/0157626 A1 | 6/2015 | Cohen et al. |
| 2016/0022992 A1 | 1/2016 | Franke et al. |
| 2019/0167134 A1 | 6/2019 | Block et al. |
| 2019/0239763 A1 | 8/2019 | Block et al. |

OTHER PUBLICATIONS

International Search Report in PCT/US2013/065968, dated Jan. 30, 2014, in 2 pages.

Written Opinion of the International Searching Authority in PCT/US2013/065968, dated Jan. 30, 2014, in 10 pages.

Ahmadian A et al., "Analysis of lumbar plexopathies and nerve injury after lateral retroperitoneal transpsoas approach: Diagnostic standardization," J Neurosurg Spine 2013; 18(3); pp. 289-297.

Silverstein J et al., "Saphenous nerve somatosensory evoked potentials: A novel technique to monitor the femoral nerve during transpsoas lateral lumbar interbody fusion," Spine (Phila Pa 1976) 2014; 39(15); pp. 1254-1260.

Robinson LR et al., "The efficacy of femoral nerve intraoperative somatosensory evoked potentials during surgical treatment of thoracolumbar fractures," Spine (Phila Pa 1976) Oct. 1, 1993; 18(13); pp. 1793-1797.

Block J et al., "Motor evoked potentials for femoral nerve protection in transpsoas lateral access surgery of the spine," Neurodiagnostic Journal, Mar. 2015; 55(1); pp. 36-45.

Chaudhary K et al., "Trans-cranial motor evoked potential detection of femoral nerve injury in trans-psoas lateral lumbar interbody fusion," Journal of Clinical Monitoring and Computing, Jun. 17, 2015, pp. 549-554.

International Search Report and Written Opinion of the International Searching Authority in PCT/US2017/042271, dated Sep. 26, 2017, in 16 pages.

International Search Report and Written Opinion of the International Searching Authority in PCT/US2017/041995, dated Sep. 28, 2017, in 8 pages.

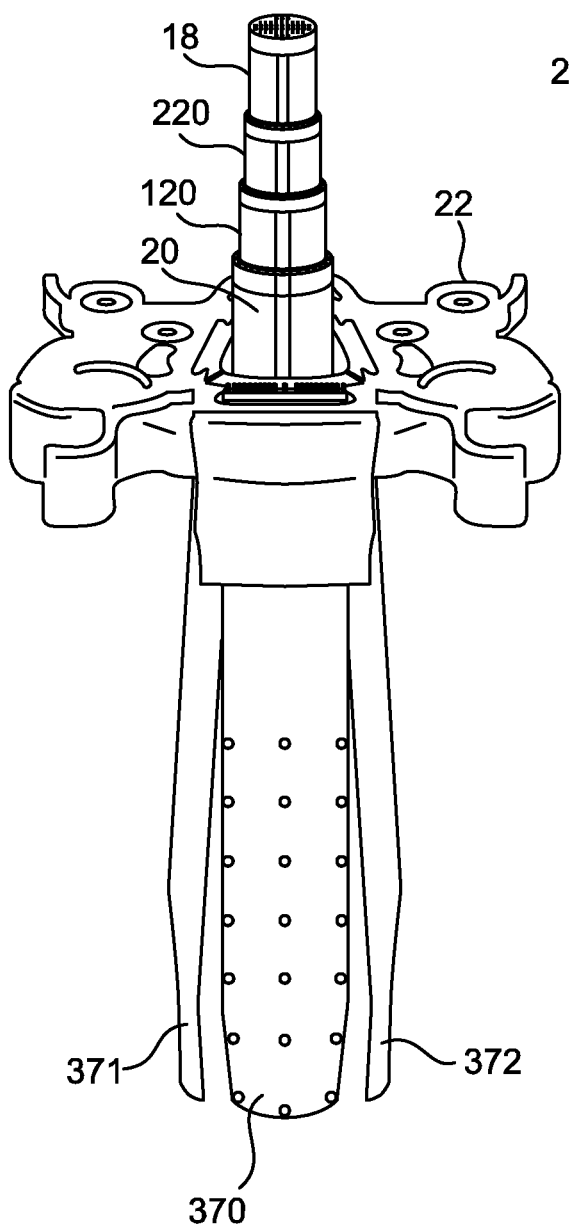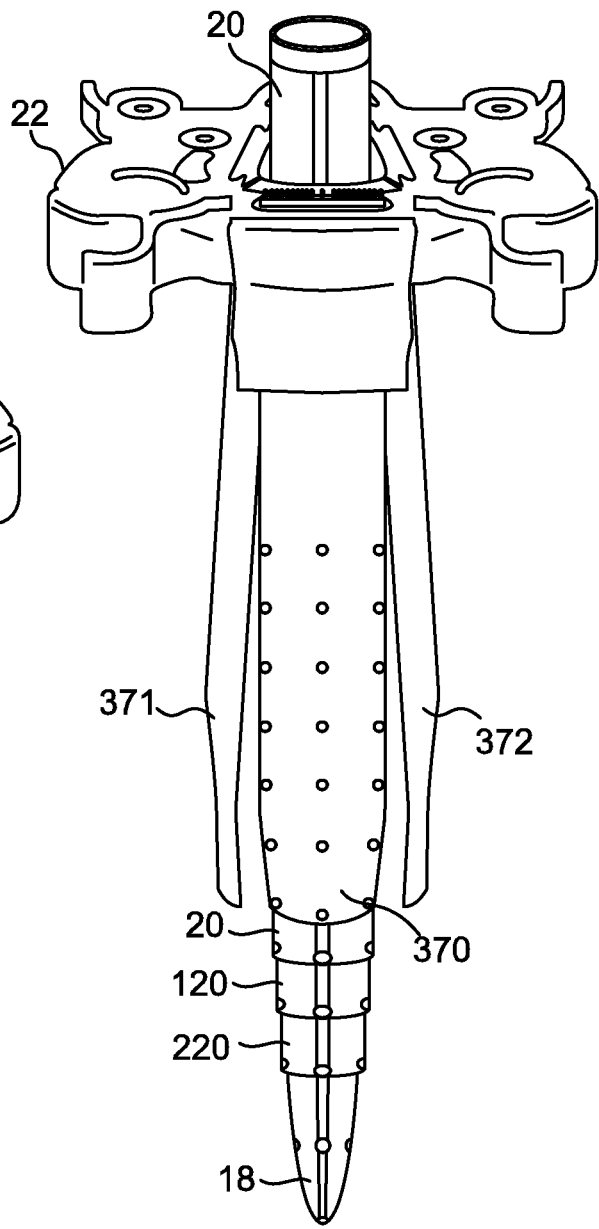
FIG. 14A
FIG. 14B

SYSTEMS AND METHODS FOR NERVE MAPPING AND MONITORING

CROSS-REFERENCE TO RELATED APPLICATIONS

This application is a continuation of U.S. patent application Ser. No. 16/025,249, filed Jul. 2, 2018, which application is a continuation of U.S. patent application Ser. No. 14/059,256, filed Oct. 21, 2013, which application claims the priority benefit of U.S. Provisional Patent Application No. 61/715,956, filed Oct. 19, 2012. The disclosures of each of the foregoing applications are hereby incorporated by reference herein in their entireties.

Any and all applications for which a foreign or domestic priority claim is identified in the Application Data Sheet as filed with the present application are hereby incorporated by reference under 37 CFR 1.57.

TECHNICAL FIELD

Embodiments of the technology relate, in general, to systems and methods for intraoperative peripheral nerve motor fiber mapping and monitoring, and in particular to systems and methods for intraoperative peripheral nerve motor fiber mapping and monitoring that can be applied to a variety of surgical instruments including but not limited to surgical probes, tissue dilators, and retractors.

BACKGROUND

Many types of nerve injury can be caused during surgical procedures, where such nerve damage can have long lasting or permanent effects. Many surgical procedures come into close contact with neural structures and these procedures have the potential to permanently harm or even kill patients. In addition to other neural damage, neurapraxia, axonotmesis, or neurotmesis can result from surgical procedures.

SUMMARY

Embodiments can include a nerve mapping and monitoring system that can include a multi-polar stimulation unit, an electrical connector that can have a first end and a second end, where the first end can be coupled with the multi-polar simulation unit, an instrument having a grid array, where the grid array can comprise a plurality of electrodes, where each of the plurality of electrodes can be configured to be stimulated by the multi-polar stimulation unit, a recording element, where the recording element can be configured to detect a muscle response elicited by the grid array, and a computer system, where the computer system can be configured to monitor the muscle response elicited by the grid array such that neural structures can be identified and avoided.

Embodiments can include a nerve mapping and monitoring system that can include a multi-polar stimulation unit, an electrical connector that can have a first end and a second end, wherein the first end is coupled with the multi-polar simulation unit, a ring connector, wherein the ring connector can be coupled with the second end of the electrical connector, an instrument having a first end and a second end, the instrument including a lower portion and an upper portion divided by a horizontal circumferential line, where the ring connector can be configured for attachment to the upper portion of the instrument, a grid array, where the grid array can be positioned on the lower portion of the instrument, where the grid array can comprise a plurality of electrodes that can be circumferentially positioned about the lower portion of the instrument, where each of the plurality of electrodes can comprise an alphanumeric notation and can be configured to be stimulated independently by the multi-polar stimulation unit. The nerve mapping and monitoring system can include a recording element, where the recording element can be configured to detect a muscle response elicited by the grid array, a computer system, where the computer system can be configured to monitor the muscle response elicited by the grid array such that neural structures can be identified and avoided, and a display, where the display can be configured to visually represent the response elicited by the grid array and monitored by the computer system.

Embodiments can include a nerve mapping and monitoring system that can include a means of generating multi-polar stimulation, a means for delivering multi-polar stimulation to a patient, a means for detecting the patient's muscle response to the multi-polar stimulation, and means for determining the location of neural structures based upon the patient's muscle response.

BRIEF DESCRIPTION OF THE DRAWINGS

The present disclosure will be more readily understood from a detailed description of some example embodiments taken in conjunction with the following figures:

FIG. 14A depicts a front perspective view of a multi-polar surgical probe associated with a multi-polar sequential dilation system and a multi-polar surgical retractor system according to one embodiment.

FIG. 14B depicts a front perspective view of the multi-polar surgical probe, the multi-polar sequential dilation system, and the multi-polar surgical retractor system of FIG. 14A, shown in an alternate configuration.

DETAILED DESCRIPTION OF THE PREFERRED EMBODIMENT

Figure 1:
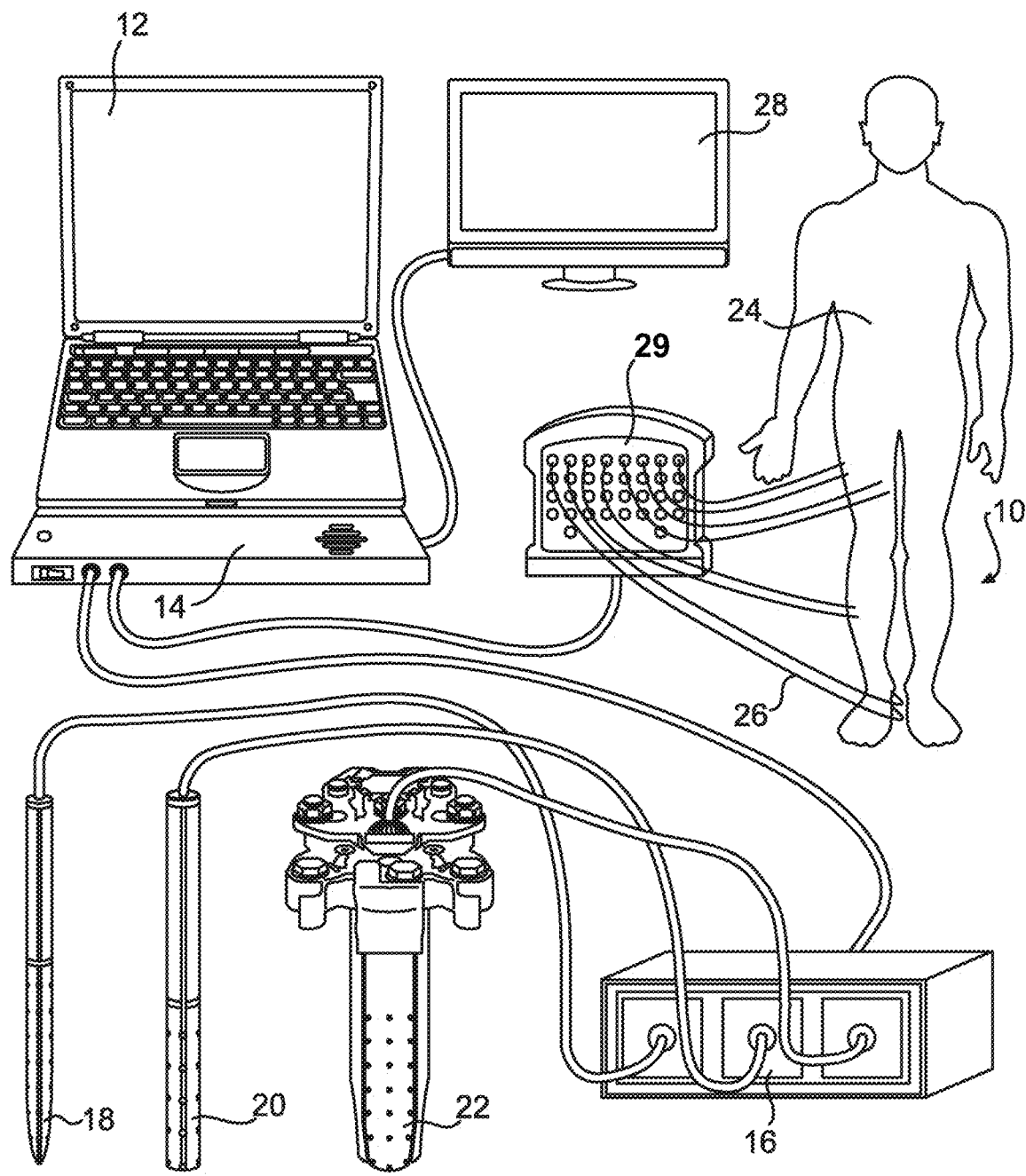
FIG. 1 depicts an example nerve monitoring and mapping system according to one embodiment.

Various non-limiting embodiments of the present disclosure will now be described to provide an overall understanding of the principles of the structure, function, and use of the proficiency tracking systems and processes disclosed herein. One of more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

Described herein are example embodiments of nerve mapping and monitoring systems and methods that can improve the safety of surgical procedures. In one example embodiment, the system can map peripheral nerves by electrically exciting a nerve or nerve root with stimulating electrodes while simultaneously recording the evoked response of the resultant electrical activity from the muscles that are innervated. In some embodiments, the electrical activity can be recorded with surface pads that can be placed on a patient's skin in close proximity to the muscles of interest.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as in indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Example embodiments described herein can assist surgeons in safely accessing deep surgical sites while preventing or minimizing the chance that neurological structures are damaged. For example, an operative corridor can be created that can reduce or prevent the likelihood that neurological damage will occur.

A nerve mapping and monitoring computer system can execute software for the operation of a surgical probe and related systems, as described in more detail below. The nerve mapping and monitoring computer system can run on any suitable computing system, such as a dedicated serve, a user computer or server, multiple computers, a collection of networked computers, a cloud-based computer system, a web-based computer system, or from a storage device, for example. One or multiple processing units, such as central processing units and/or graphics processing units, may perform instructions stored in memory to execute the processes described therein.

A nerve mapping and monitoring computer system in accordance with the present disclosure can be accessed via any suitable technique, such as a web-browser such as SAFARI, OPERA, GOOGLE CHROME, INTERNET EXPLORER, or the like executing on a client device. In some embodiments, the systems and methods described herein can be a web-based application or a stand-alone executable. Additionally, in some embodiments, the systems and methods described herein can integrate with various types of nerve mapping and monitoring systems, such as multi-polar stimulation probes tissue dilator systems, wiring systems, mono-polar system, bi-polar systems, needle electrodes, surface pads, tri-polar systems, and the like. Any suitable client device can be used to access, or execute, the nerve mapping and monitoring computer systems computing system, such as laptop computers, desktop computers, smart phones, tablet computers, gaming system, and the like.

Systems and methods described herein may generally provide a safe environment for users (e.g., surgeons) to perform surgical procedures with a reduced risk of neurological damage. Interaction with the nerve mapping and monitoring system may include, without limitation, keyboard entry, writing from pen, stylus, finger, or the like, with a computer mouse, or other forms of input (voice recognition, etc.). The information or data related to the mapping or monitoring may be presented on a tablet, desktop, phone, board, or paper, or in any suitable manner. In one embodiment, the user may interact with a mapping and monitoring system by writing with a smart pen on normal paper, modified paper, or a hard flat surface or their preference. In this embodiment, the user may receive real-time feedback, or at least near real-time feedback, or may synchronize with a nerve mapping and monitoring computer system at a later date. The nerve mapping and monitoring computer system can include a personal computer, one or multiple computers in server-type system, or any other suitable arrangement.

User interaction with the nerve mapping and monitoring computer system may take place in any of a variety of operational environments, such as a hospital setting or clinical setting, with one or more users interacting with the system at a given time. Versions describe herein include systems and methods for intraoperative peripheral nerve motor fiber mapping and monitoring which can be applied to a variety of surgical instruments including but not limited to surgical probes, tissue dilators, and retractors. Such systems and methods can provide a surgeon with useful information intraoperatively including alerting the surgeon to the presence of neural structures in a surgical field, providing information about the relative direction and location of neural structures in the surgical field, provide quantitative estimates of the proximity of neural structures in relation to the surgical equipment, and providing continuous monitoring of the function of neural structures in the surgical field.

Versions described herein can be aimed at assisting surgeons in providing safer surgery for a variety of procedures that can involve creating an operative corridor from the skin surface to a given deep surgical target site. Creation and maintenance of a surgical corridor can involve passing in close proximity to various neural structures. Damage to these neural structures can result in post-operative neurological impairments which may range from mild transient motor and sensory disturbances to severe, permanent motor paralysis and/or post-operative intractable pain or paresthesias. Prevention of neurological damage in surgery is important as the consequences of these complications can be devastating to patients and costly and difficult to treat post-operatively. Embodiments described herein can assist the surgeon in safely accessing deep surgical sites while preventing damage to neurological structures. Versions described herein can improve the resolution and accuracy of neurophysiological recordings compared to existing systems and methods of intraoperative nerve mapping and monitoring and can increase the surface area of the operative corridor which can be monitored and protected.

Neuromonitoring and mapping of peripheral nerves can include electrically exciting a nerve/nerve root with stimulating electrodes (such as a single anode and cathode) while simultaneously recording the evoked response of the resultant electrical activity from the muscle(s) that are innervated by that nerve with standard electromyography techniques. Recording of the evoked responses can be performed with, for example, surface pads on the skin over the muscle or with needle electrodes embedded within or in close proximity to the muscle or muscles of interest.

With electrical stimulation of a peripheral nerve/nerve root, the minimal amount of electrical current required to elicit a muscle response can be termed the "motor threshold" (which can be measured in milliamps). The act of determining the minimum amount of current to elicit a motor response in a gen muscle is generally termed "motor response thresholding". Motor thresholding can help make quantitative estimates of the proximity of motor nerve fibers in the surgical field based on the amount of current delivered to the stimulating electrodes (measured in milliamps). The theory is based on the generally accepted premise that the motor threshold is directly proportional to the proximity of the stimulating electrodes to the nervous tissue. In other words, the lower the amount of current required to elicit a motor response, the closer the stimulating electrodes are to the nerve. For example, a motor threshold response in a given muscle from electrical stimulation at 2 mA of current can suggest that the stimulating electrodes are in closer proximity to a nerve in comparison to a motor threshold response at 12 mA.

Embodiments described herein can include a software driven electrical stimulation system that can deliver precisely controlled electrical stimulation to various combinations of electrodes that can be located on a grid array of electrodes fixed on to various types of surgical equipment such as, for example, a probe, tissue dilator, retractor, or the like. The grid array of electrodes, whether in a wand-like probe, cylindrical shaped probe, or incorporated into retractor blades, can afford accurate and precise monitoring in three-dimensional space throughout the depth and surface(s) of soft and hard anatomical structures (e.g., muscle such as psoas, brain tissue). A computer can direct an external electrical power source to systematically provide controlled, focal electrical stimulation sequentially to varying sets of electrodes on the grid. Any electrically evoked muscle responses from each of the sets of electrodes can be recorded and the amount of electrical current required to elicit each muscle response can be obtained with standard electromyography (EMG) techniques. A display of the results can alert a surgeon to the presence of neural structures in relation to each particular electrode on the grid (mapping). In addition, the amount of stimulation required to elicit a response (motor threshold) of each set of electrodes can provide quantitative estimates about the proximity of the electrodes on the grid to each specific electrode on the grid. A color coded virtual "map" of these threshold values can be displayed to illustrate the presence, proximity, and/or direction of neural structures in the surgical field in relation to the surgical equipment.

In addition, the functional status of neurological structures encountered in the surgical field can be obtained throughout the duration of the procedure (neuromonitoring). Changes in the characteristics of the electrically evoked motor responses (as compared to baseline values) can alert the surgeon of possible impending neurological damage. Such changes in the evoked muscle responses with peripheral nerve/root electrical stimulation are described in various texts and are commonly utilized in intraoperative peripheral nerve monitoring. Examples of these variables may include changes in the evoked muscle response morphology, latency, slope and the amount of current required to elicit a response.

Referring now to FIG. 1, one embodiment a nerve mapping and monitoring system 10 is shown. The nerve mapping and monitoring system 10 can be controlled by specifically designed software controlled by a laptop or computer 12. The computer 12 can be connected to a differential amplifier or main control box 14 which can be built specifically for this purpose or the system can be used with an existing commercially available differential amplifier. If this system is utilized with an existing commercially available differential amplifier, additional software can be provided that can allow for utilization of a multi-polar stimulation unit 16. The multi-polar stimulation unit 16 can provide software controlled electrical stimulation independently, for example, to each electrode on the grid of any surgical instrument fitted with a multi-polar electrical grid. Such instruments can include, but are not limited to, a surgical probe 18, a tissue dilator 20 or a retractor system 22. Different grid layouts can be applied to each specific piece of surgical equipment and the software controlling the electrical stimulation and recording can be specifically programmed for each particular grid.

A patient 24 can be fitted with a recording needle or surface electrodes 26 in multiple muscles of interest. The recording electrodes 26 can be connected to a pre-amplifier 29 such as is commonly used in intraoperative EMG recording systems. The pre-amplifier 29 can be connected to the main base unit containing a differential amplifier or main control box 14 that can integrate the EMG recordings with the electrical stimulation.

The software can be designed to control the multi-polar stimulation unit 16 to sequentially deliver precise amounts of electrical current to varying sets of electrodes on the grid while simultaneously recording any motor responses with the pre-amplifier 29 and main control box 14 with standard electromyography recording techniques. The software can be designed to detect the presence of any muscle responses recorded following each electrical stimulation. Sequential electrical stimulations of varying sets of electrodes on the grid can illustrate which sets of electrodes elicit motor responses and which sets of electrodes do not. The lowest level of electrical stimulation required to obtain a motor response from each set of electrodes can be recorded (e.g., the motor threshold level). Once this information is obtained from multiple stimulations of multiple sets of electrodes on the grid, the software can generate a color coded map, or other visual display, of the grid correlating to the levels of electrical stimulation required to elicit motor responses from each electrode. A virtual representation of the grid can be displayed for the surgeon to view on a monitor 28. The "virtual map" can provide vital information to assist the surgeon in navigating around neural structures and thus avoiding damage.

The presence of absence of electrically evoked motor responses from stimulation of sets of electrodes on the grid can be recorded, color coded, and presented on monitor 28. Evoked muscle responses generated at low electrical stimulation levels (low threshold responses) can be color coded as progressively darker shades of red, signifying a warning of close proximity to neural structures. Motor responses evoked at relatively higher stimulation levels can be designated in shades of yellow signifying caution relating to the presence of neural structures near the specific stimulating electrodes on the grid. Absent motor responses at even higher stimulation levels can be color coded as green signifying an absence of motor neural structures in proximity to the specific electrodes on the grid. This "traffic light" color coding system can be utilized to inform the surgeon of the presence and/or proximity of neural structures in relation to each electrode on the grid and can help create a useful navigational map of the surgical field. It will be appreciated that any suitable visual, tactile, and/or auditory display or feedback is contemplated. The actual stimulation threshold levels (which can be measured in mA) that evoke motor responses that are to be designated by the software to be displayed as red, yellow or green, can be based on the relative motor threshold values obtained in vivo, or the threshold values that correlate to a particular color can be pre-programmed based on clinical experience or the results of experimental studies, such as animal models.

Figure 13:
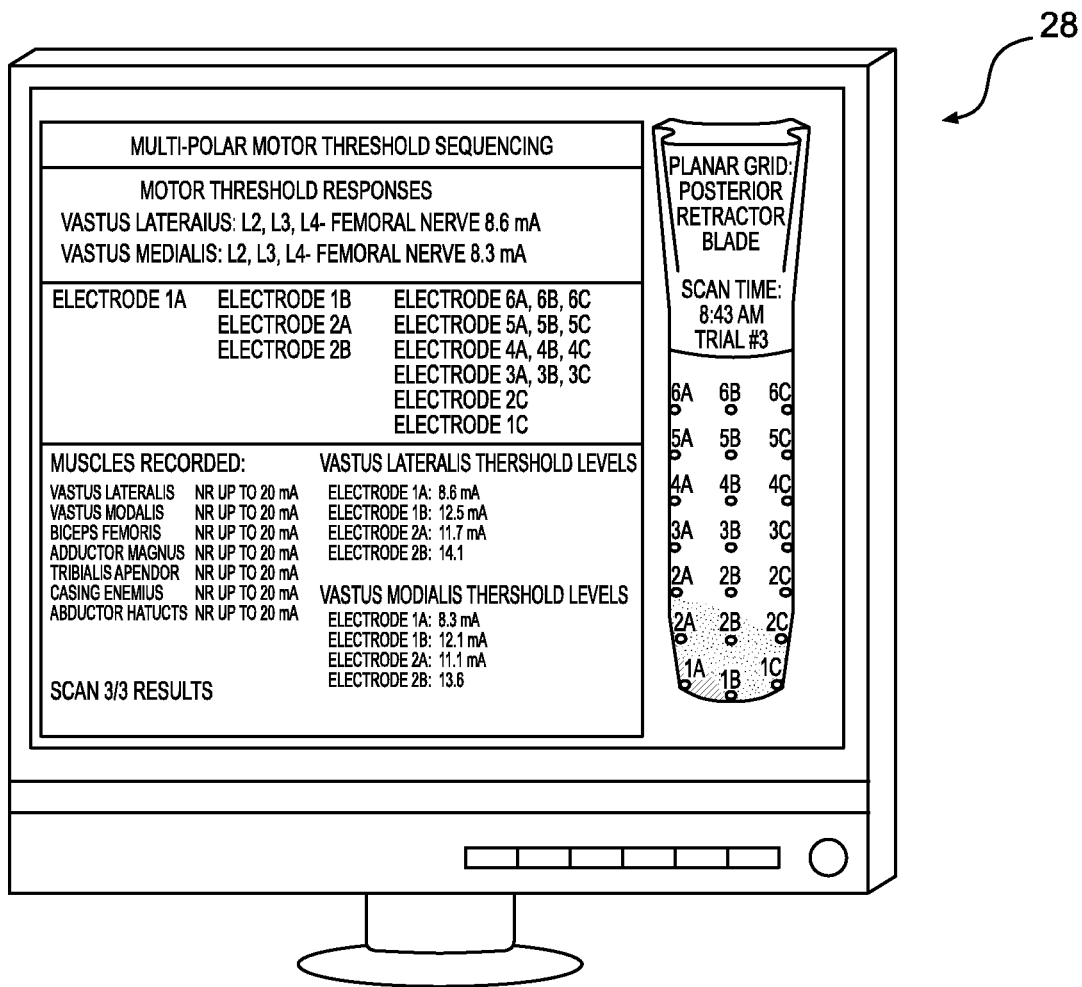
FIG. 13 depicts a front perspective view of a display for a system according to one embodiment.

In some embodiments, referring to FIG. 13, the monitor 28 can display the results of a multi-polar threshold sequencing run with a multi-polar planar grid on a retractor blade. The lowest threshold electrically evoked motor responses can be seen with electrical stimulations involving electrode #1A. In this example, motor evoked responses from stimulation with electrode #1A are observed in the vastus lateralis and vastus medialis muscles at 8.6 mA and 8.3 mA respectively.

The example of a virtual map can provide important information to the surgeon including informing the surgeon of the presence of neural structures in the surgical field or giving the surgeon an idea of which particular neural structures are present. In this example, it is likely that the retractor is near the lumbar nerve roots (L2, L3, or L4) or the femoral nerve. The nerve mapping and monitoring system 10 can provide information regarding the direction of neural structures in the field (nearest to the left distal tip of the retractor), can give information regarding the relative proximity of a retractor to the neural structure as evidenced by the relatively low amount of current (8.3-8.6 mA) required to elicit a threshold motor response, and can provide information illustrating an absence of detectable motor nerve fibers in proximity of the remainder of the retractor blade surface (green areas).

Figures 2A, 2B:
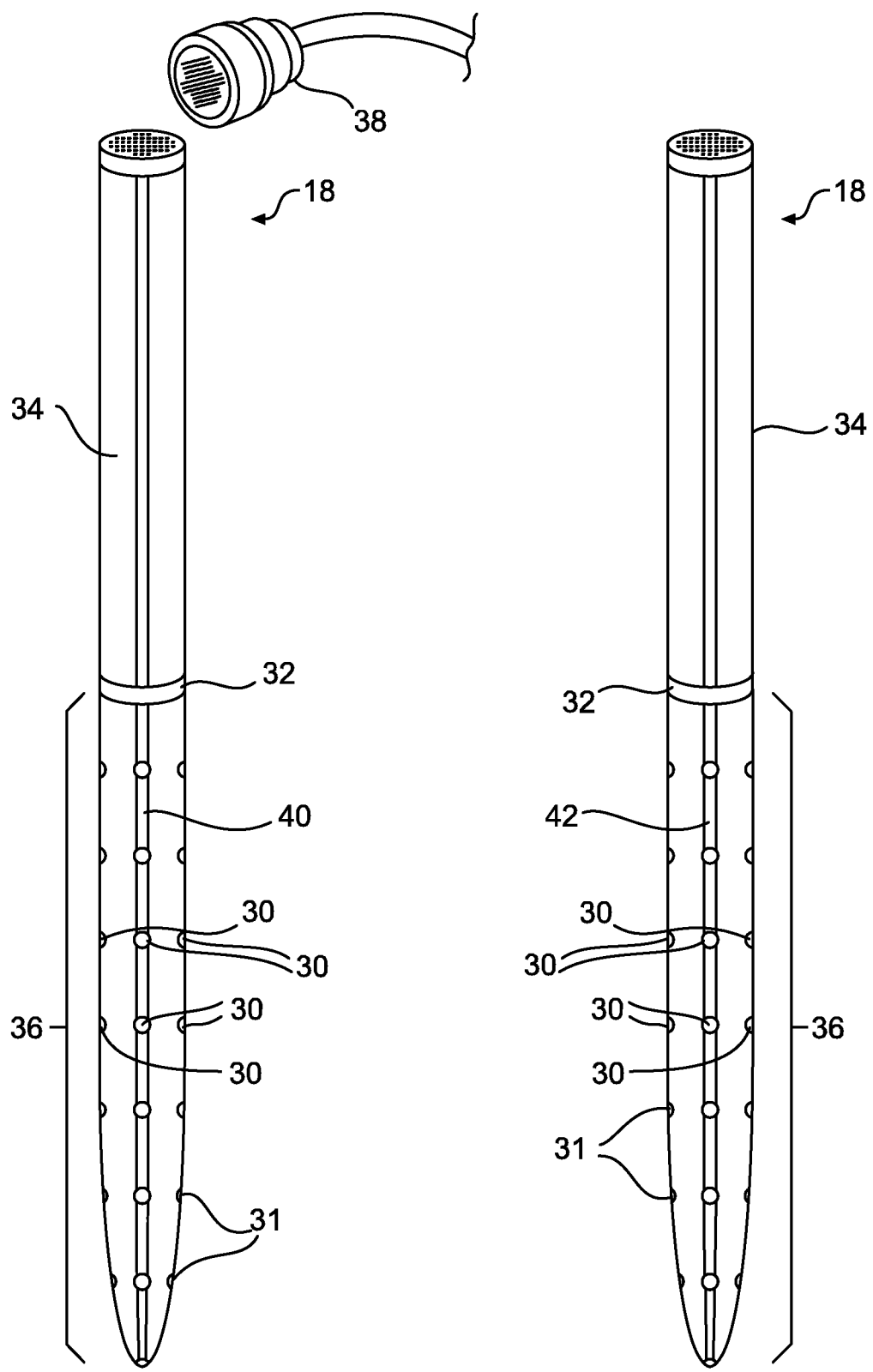
FIG. 2A depicts a front perspective view of a handheld surgical probe and connector of a wiring system according to one embodiment.
FIG. 2B depicts a rear perspective view of the handheld surgical probe show in FIG. 2A.

FIGS. 2A and 2B depict a version of a handheld surgical probe 18 that can be made of an electrically insulating material and can be fitted with a grid 30 of electrodes. The grid 30 of electrodes can be arranged circumferentially around the probe with equidistant spacing between the electrode surfaces. The optimal number, size, shape and configuration of the electrodes on the grid can vary according to the particular surgical requirements. The optimal electrode configuration may be determined experimentally or by mathematical modeling, for example.

A horizontal circumferential line 32 can separate the handle area 34 located above the line where a surgeon can safely touch and maneuver the probe surgical probe 18. An effective electrical stimulation area 36 can contain the grid 30 of electrodes and can be located below the horizontal circumferential line 32. An electrical pin connector 38 can connect the external multi-polar stimulation unit 16 to the electrical contact ports located at the top of the surgical probe 18. An anterior orientation line 40, can provide a reference point on the probe relative to the surgical field. The anterior orientation line could be colored for contrast for easy recognition within in the surgical field. The anterior orientation line 40 can be considered to be at a "12 o'clock position" or considered "north" to designate its relative position in the surgical field. A posterior orientation line 42, which can be colored differently to distinguish it from the anterior orientation line 40, can be placed in a position 180° from the anterior orientation line 40. This posterior orientation line 42 can be considered to be located at a "6 O'clock" position or "south" relative to the surgical field.

Figure 3A:
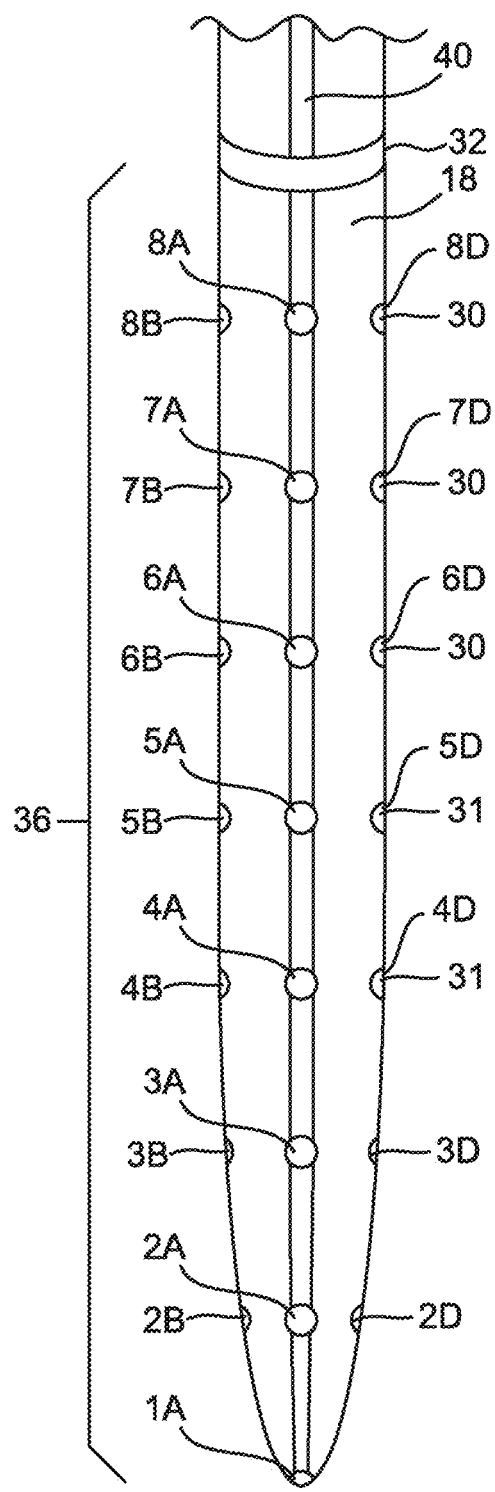
FIG. 3A depicts a partial magnified view of the handheld surgical probe shown in FIG. 2A.
Figure 3B:
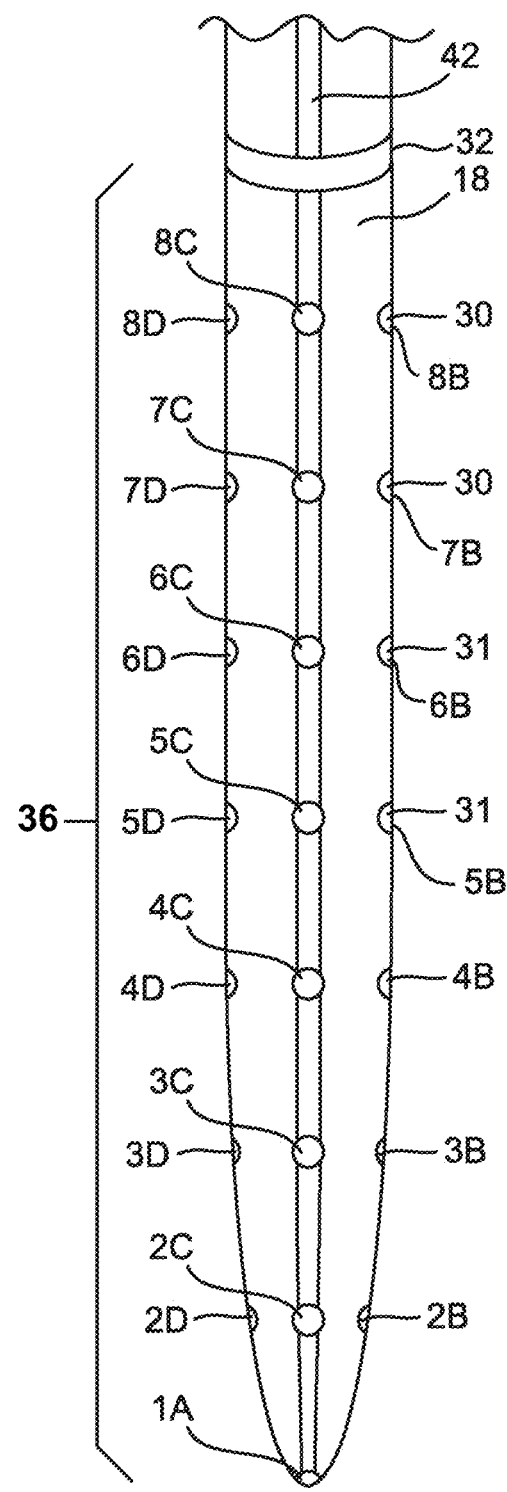
FIG. 3B depicts a partial magnified view of the handheld surgical probe shown in FIG. 2B.

Referring to FIGS. 3A and 3B, an example of the configuration and nomenclature of a circumferential electrode grid 30 on a surgical probe 18 is shown. The grid 30 of stimulating electrodes can be placed, for example, equidistantly and circumferentially around the surgical probe 18 to obtain an effective 360° of stimulating surface along the length of the effective electrical stimulation area 36 of the surgical probe 18. Electrodes 31 in the grid 30 can be designated with alphanumeric names by their orientation on the probe depending on their position on each column and row of the grid.

In one version, the designation of alphanumeric names of each particular electrode 31 can direct the software to control the delivery of precisely controlled electrical stimulation from the multi-polar stimulation unit 16 independently to each electrode 31 on the grid 30 as is described in greater detail with reference to multi-polar electrical stimulation sequencing of peripheral nerves/roots with sequential motor thresholding using circumferential and planar grid arrays.

As illustrated in FIGS. 3A and 3B, rows or the vertical positions of electrodes 31 can be numbered starting with #1 at the most distal tip of the surgical probe 18. In the example configuration provided, there are 8 rows with the #1 electrode at the most distal tip of the surgical probe 18 with subsequent numbering of the rows of electrodes continuing upward with the row #8 electrodes 31 being located at the uppermost portion of the stimulating area 36 of the surgical probe 18. The actual number of stimulating electrodes 31 on any given grid 30 can vary according to particular surgical requirements. For an electrified surgical probe, it may be advantageous to have only a single electrode at the distal tip however different electrode configurations may be found to be more effective.

The columns or horizontal positions of electrodes can be lettered starting with the "A" electrode of each column located directly on the middle of the colored anterior orientation line 40. Subsequent electrodes in each column can be designated alphabetically in a clockwise direction around the circumference of the surgical probe 18 for each column. In the example illustration provided, each column (except for row 1) has 4 electrodes named A, B, C, and D, sequentially designated in a clockwise direction. In this illustration, the "A" electrode in each column is located on the anterior orientation line 40. The A electrode can be also referred to as the "North" electrode. The "B" electrode in each column is located 90° clockwise to the "A" electrode at a 3 o'clock position (or referred to as the "East" electrode). The "C" electrode in each column is located 180° from the "A" electrode on the posterior orientation 42 (which could be colored differently than the anterior orientation line 40). The posterior orientation line 42 can designate a "6 o'clock" or a "South" position. The "D" electrode in each column is located in a position 270° clockwise from the "A" electrode (located at 9 O'clock or considered "West"). These references to a clock or a compass are common ways of assisting in directional orientation and can be helpful to assist the surgeon to quickly comprehend the relative location of neural structures within the surgical field relative to the anterior orientation line 40.

In the illustrated example, a twenty-nine electrode 31 grid 30 montage on a circumferential multi-polar surgical probe 18 is shown. The nomenclature for each electrode can contain a designation of the row (1, 2, 3, 4, 5, 6, 7 and 8) (numbered from the distal tip of the probe towards the top) and can be followed by a designation of the column (A, B, C & D) (lettered alphabetically clockwise from the anterior orientation line). It will be appreciated that any suitable electrode orientation, any suitable electrode number, and any suitable nomenclature, marking, or identifying is contemplated.

Figure 4:
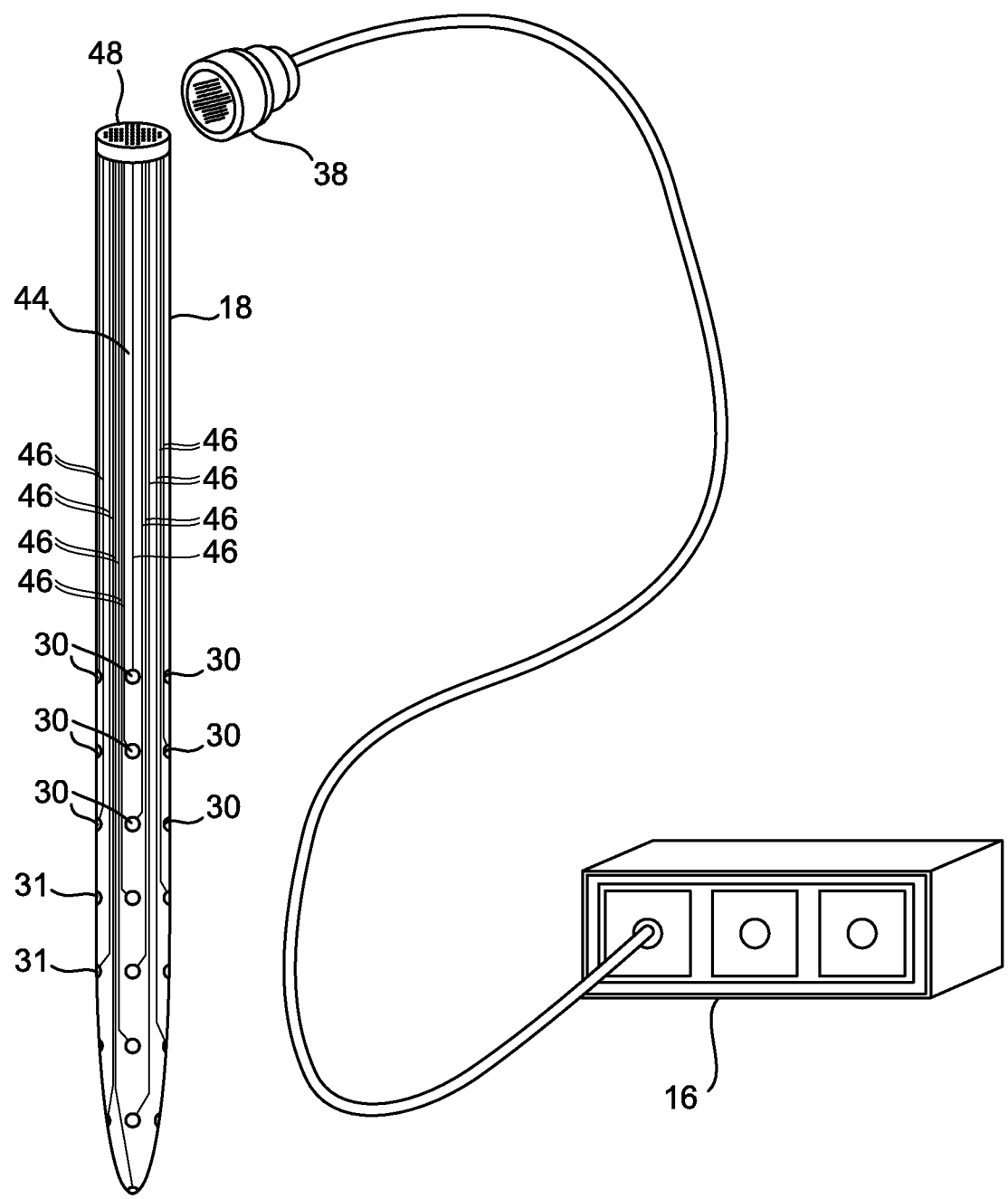
FIG. 4 depicts front perspective view of a surgical probe and a perspective view of an associated wiring system according to one embodiment.

Referring to FIG. 4, one version of an electrical grid 44 is shown that can be wired on the multi-polar surgical probe 18. Each electrode 31 can be wired with wires 46 directly and independently of the other electrodes to provide precisely controlled, focal electrical stimulation to each electrode 31 on the grid 30. An electrical pin connector 38 can connect the external multi-polar stimulating unit 16 to the electrical contact connector ports 48 located at the top of the surgical probe 18. It will be appreciated that any suitable electrical coupling or power source is contemplated.

Sequential tube dilation systems can utilize sequential dilation of a percutaneous tissue opening with successively larger diameter dilators to access a surgical site in order to limit collateral tissue damage.

Figures 5A, 5B:
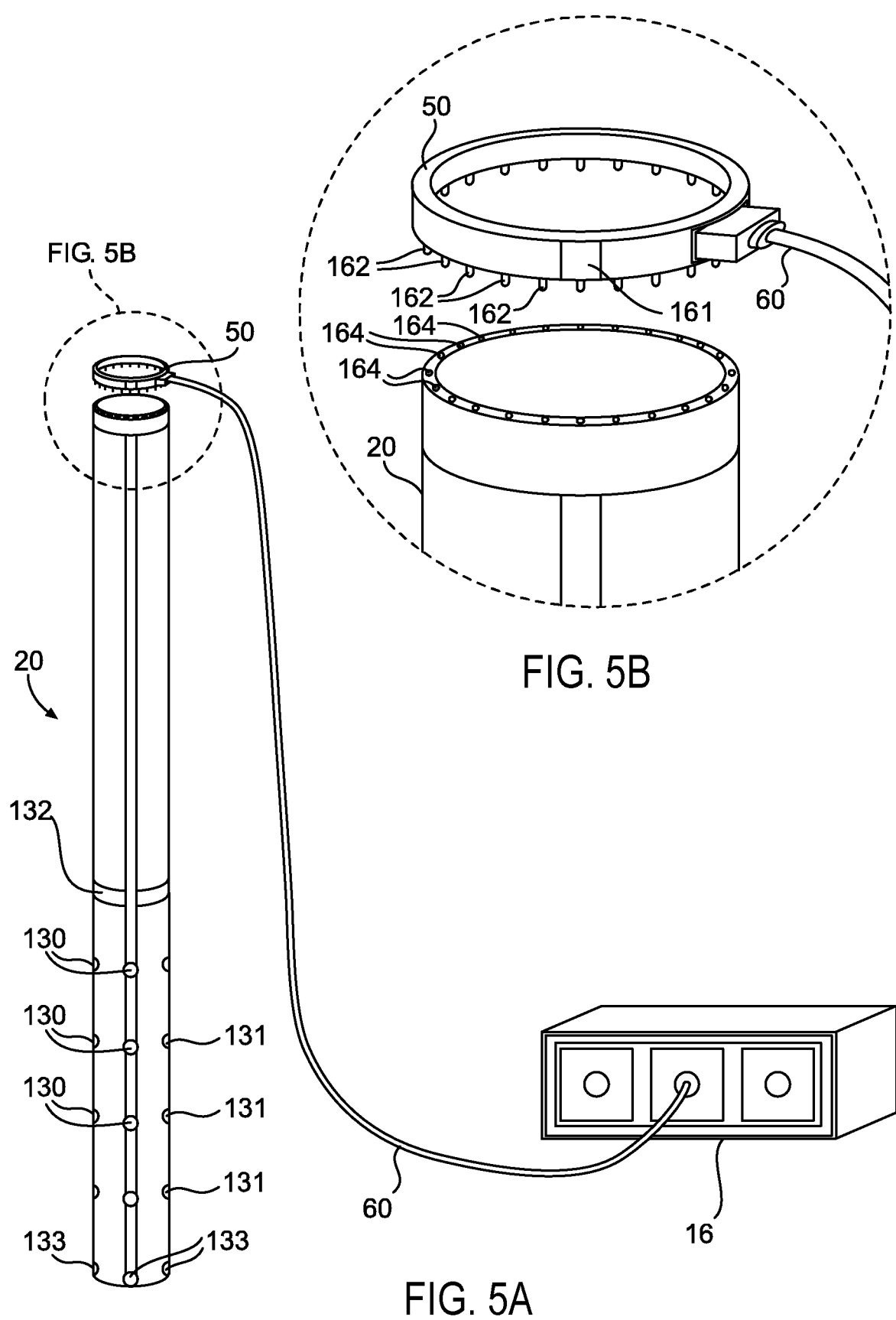
FIG. 5A depicts a front perspective view of a surgical probe associated with an electrical ring connector according to one embodiment.
FIG. 5B depicts a partial magnified view of the electrical ring connector shown in FIG. 5A.

FIGS. 5A and 5B illustrate one version of a circumferential multi-polar grid array associated with a tissue dilator system 20. The orientation lines 132 on the dilator system 20 can be the same as described with respect to the multi-polar surgical probe 18. The grid array 130 utilized on the tissue dilator system 20 can generally be the same as the multi-polar surgical probe 18 except that the 1st row of electrodes 133 on the tissue dilator system 20 can contain multiple electrodes 131 in comparison to the multi-polar surgical probe 18 which may contains a single electrode in row #1 at the distal tip of the surgical probe 18. An electrical ring connector 50 can be used to couple the electrical power source of the multi-polar stimulation unit 16 to the grid electrode array 131. The electrical ring connector can be coupled to the multi-polar stimulation unit 16 with a wire 60, or any other suitable connection. Referring to FIG. 5B, the electrical ring connector 50 can include an annular band 161 having a plurality of projections 162 that can be configured to engage a plurality of corresponding slots 164 in the dilator system 20.

Figure 6A:
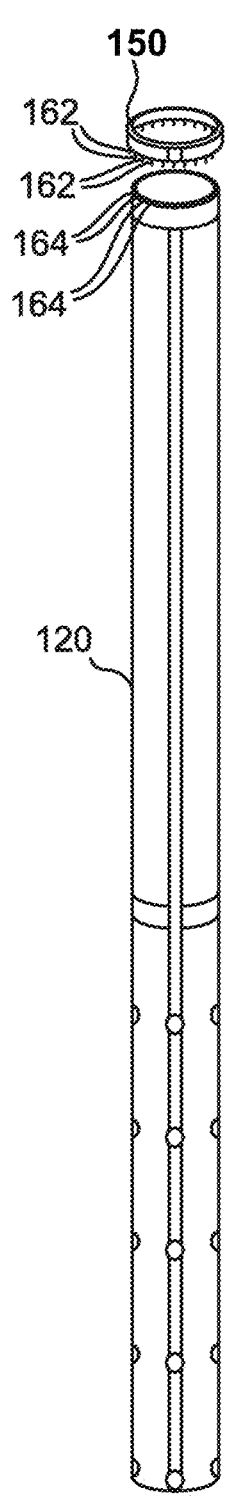
FIG. 6A depicts a front perspective view of surgical probe according to one embodiment.
Figure 6B:
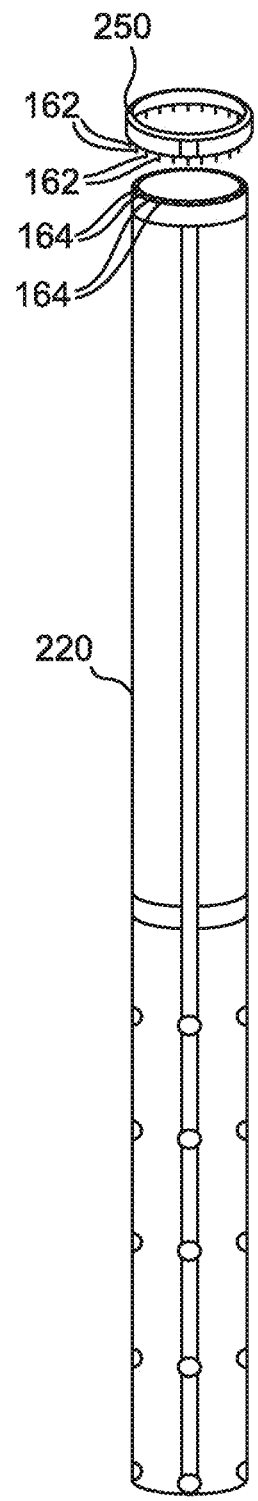
FIG. 6B depicts a front perspective view of surgical probe according to an alternate embodiments.
Figure 6C:
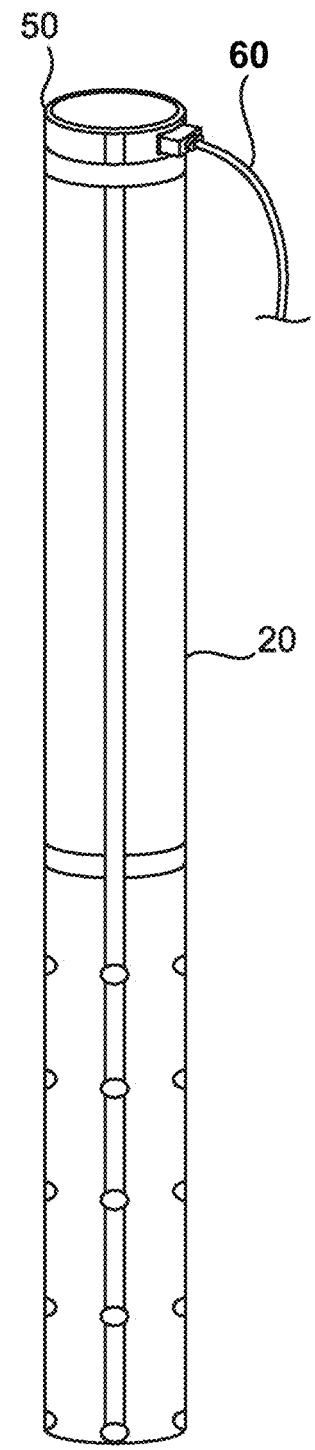
FIG. 6C depicts a front perspective view of the surgical probe shown in FIG. 5A.

FIGS. 6A-6B illustrate an example of three different sizes of tube dilator systems 20, 120, 220 that can be used for sequential dilation with the largest diameter dilator system 20, a medium size dilator system 220 and a small diameter dilator 120. The dilator system 20 can be associated with the electrical ring connector 50, the medium size dilator system 220 can be associated with an electrical ring connector 250, and the small diameter dilator 120 can be associated with an electrical ring connector 150.

Figure 7A:
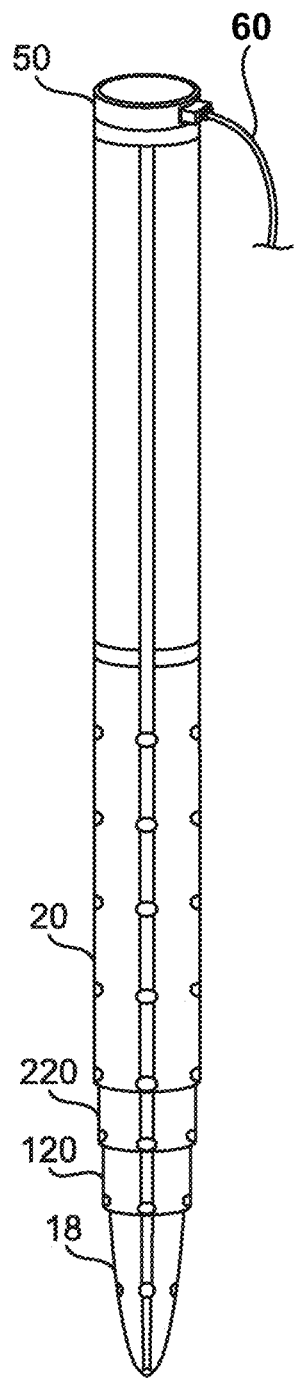
FIG. 7A depicts a font perspective view of a surgical sequential dilation system that can fit multiple tube dilators over one another to sequentially create a surgical corridor according to one embodiment.
Figure 7B:
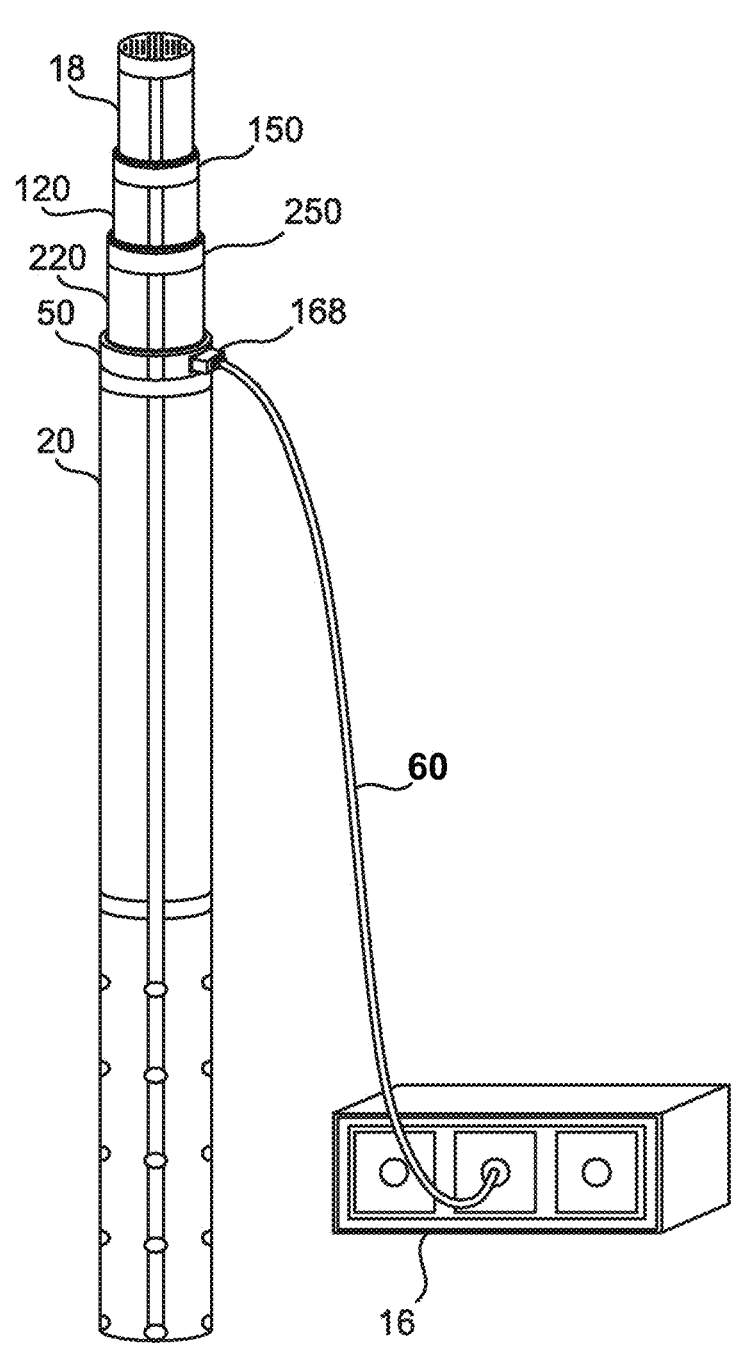
FIG. 7B depicts a front perspective view of the surgical sequential dilation system shown in FIG. 7A shown in association with a multi-polar stimulation unit.

FIGS. 7A and 7B illustrate one version of how a surgical sequential dilation system can include multiple tube dilators 20, 120, 220 positioned over one another to sequentially create a surgical corridor following confirmation of the correct initial positioning and confirmation of safe access with the multi-polar surgical probe 18. Each sequentially larger size dilator system 20, 120, 220 can slide easily over a smaller diameter tube dilator system or probe 18. The tube dilator systems 20, 120, 220 can also define a hollow lumen that can allow access for surgical instruments once a corridor is created.

Figure 8:
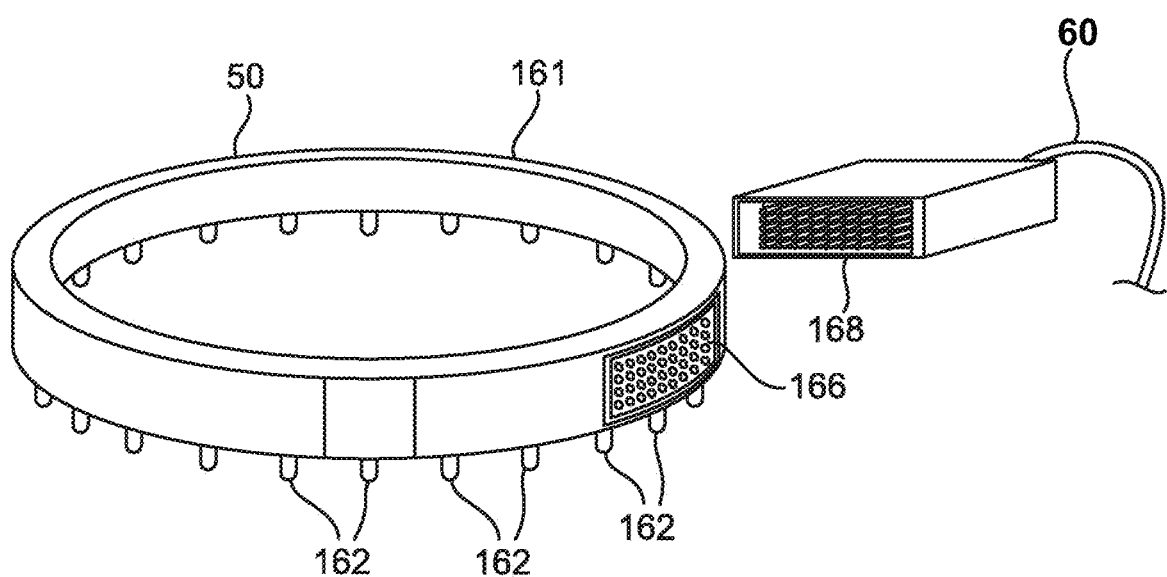
FIG. 8 depicts a front perspective view of an electrical ring connector associated with a surgical probe according to one embodiment.

Referring to FIG. 8, one example of a connection for the electrical power source of the multi-polar stimulation unit 16 to the dilator 20 can be to use an electrical ring connector 50. The electrical ring connector 50 can have a female-type electrical input port 166 that can be configured to receive a removable electrical plug connector 168 with male type electrical pin connectors. The removable electrical plug connector 166 can fit into all the different diameter ring connectors 50, 150, 250, for example. FIG. 8 illustrates one version of the electrical ring connector 50. The inferior portion of the ring connector 50 can be fitted with electrical male type electrical contacts 162 to connect the electrical wiring with female ports 164 in the dilator system 20. These connections can electrically couple the electrical ring connector 50 to the electrical wiring 46 of the tube dilator system 20 and can deliver current to each electrode 31 on the electrical grid 30 without restricting functionality. An orientation line on the ring electrode connector can be utilized to properly align the ring connectors with the correct electrical contacts. This ring connector system is only an example of how to design an electrical connection from the power source of the multi-polar stimulation unit 16 to the electrical grid 30 without interfering with the functionality of the dilator systems 20, 120, 220. Any other suitable designs or configurations of electrical connections can be utilized.

Figures 9A, 9B:
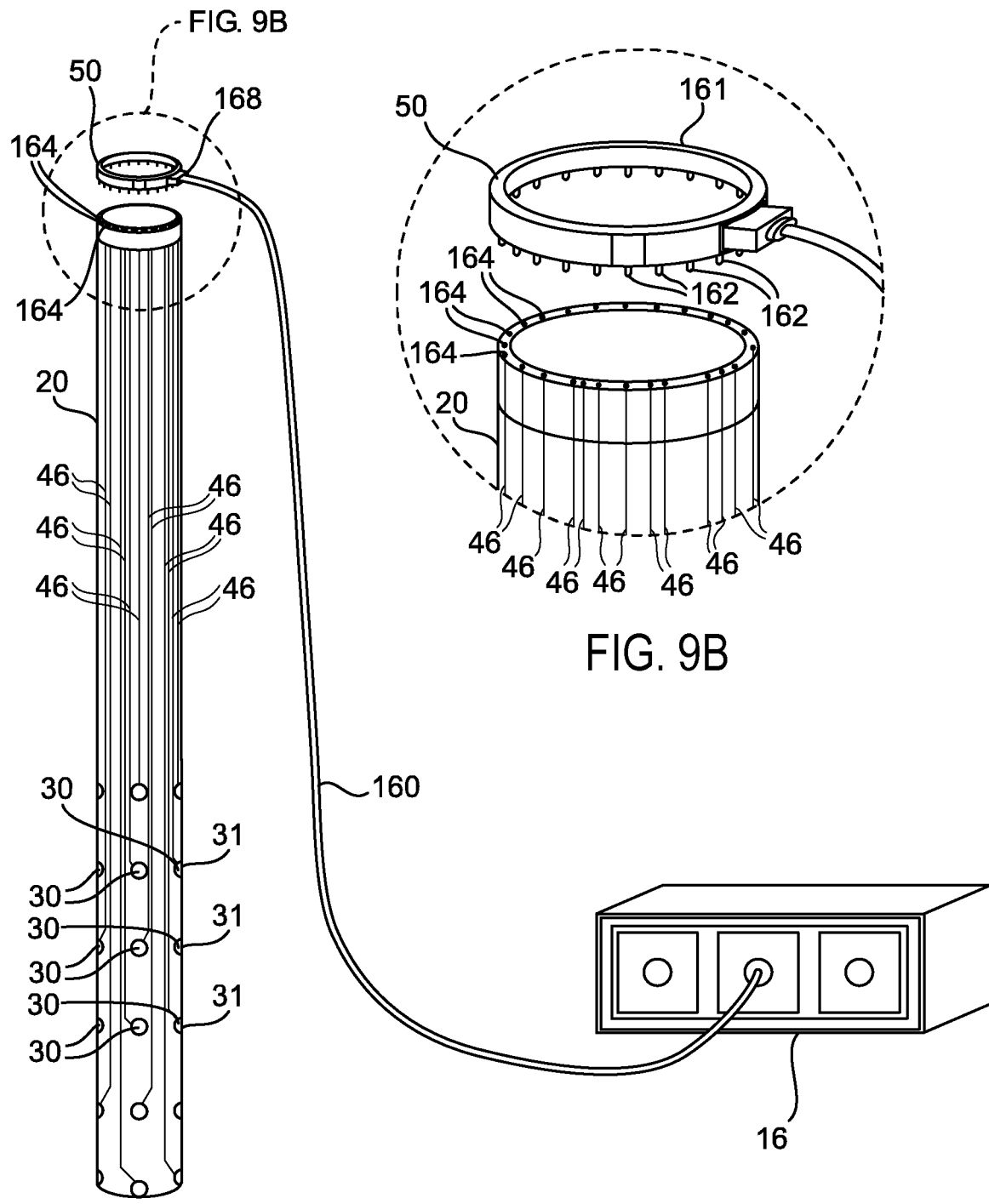
FIG. 9A depicts a front perspective view of a surgical probe associated with an electrical ring connector and a perspective view of an associated wiring system according to one embodiment.
FIG. 9B depicts a partial magnified view of the electrical ring connector shown in FIG. 9A.

FIG. 9 illustrates one version of how the electrical grid 30 can be wired on the multi-polar dilator system 20. Each electrode 31 can be electrically wired 46 directly and independently of the other electrodes to provide precisely controlled, focal electrical stimulation to each electrode on the grid 30 as is described in the section on multi-polar electrical stimulation sequencing of peripheral nerves/roots with sequential motor thresholding using circumferential and planar grid arrays.

Figure 10:
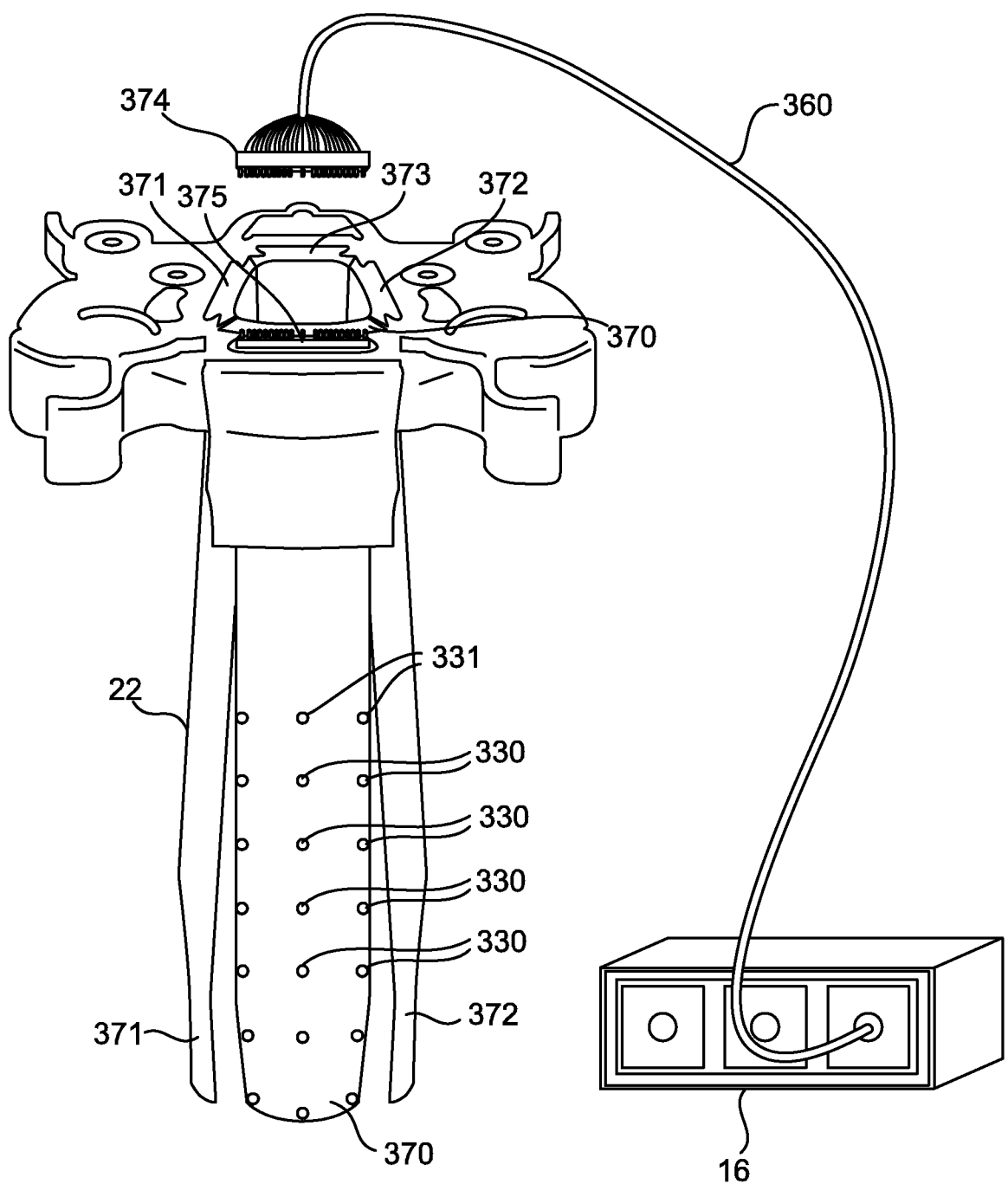
FIG. 10 depicts a front perspective view of a retractor system that can be fitted with a multi-polar grid electrode system according to one embodiment.

Referring to FIG. 10, surgical retractor systems can create and maintain a surgical corridor to access deep surgical target sites. In one version, a multi-polar sequencing grid array applied to a surgical retractor system can assist in providing safe surgical access, mapping of neural structures within the surgical field, and/or continuous functional neuromonitoring throughout a surgical procedure.

Similar principles that have been described for multi-polar stimulation in a circumferential grid array for the multi-polar surgical probe and the multi-polar tube dilation system can be applied to a planar grid array (a single plane of stimulating surface as opposed to 360° of stimulating on the circumferential grid array). In the planar configuration, the grid electrode array can be fixed on the surface of a blade of a surgical retractor where, for example. FIG. 10 illustrates a retractor system 22 that can be fitted with a multi-polar grid 330 electrode system comprises of electrodes 331 on the primary retractor blade. The base unit of the retractor system 22 can accept four separate removable retractor blades 370, 371, 372, 373, which can be moved independently to create a surgical corridor. In the example illustration provided, only the primary retractor blade 370 can be outfitted with a multi-polar grid 330 array system for the same of simplicity, however, in practice any or all of the retractor blades can be fitted with a multi-polar grid array. In one example of the retractor system 22, there can be four retractor blades. A primary or anterior retractor blade 370 with the grid 330 electrode blade 370, two lateral retractor blades 371, 372 and a secondary or posterior retractor blade 373 can be included. A removable electrical pin connector 374 can be attached to an electrical power cord 360 to couple the electrical power source of the multi-polar stimulation unit 16 to the multi-polar grid 330 on the primary retractor blade 370 via an electrical port connection 375 that can be located at the top of the retractor blade. This can be seen in more detail in FIGS. 11A-C which illustrate one version of the primary retractor blade 370 along with a schematic of the electrical wiring 346 and connections 374, 375 which can connect the multi-polar stimulation unit 16 to power the grid 330 electrode array. The magnified area shows how these connections can utilize a typical male-female electrical contact connector that can be located at the top of the retractor blade 370.

Figure 11:
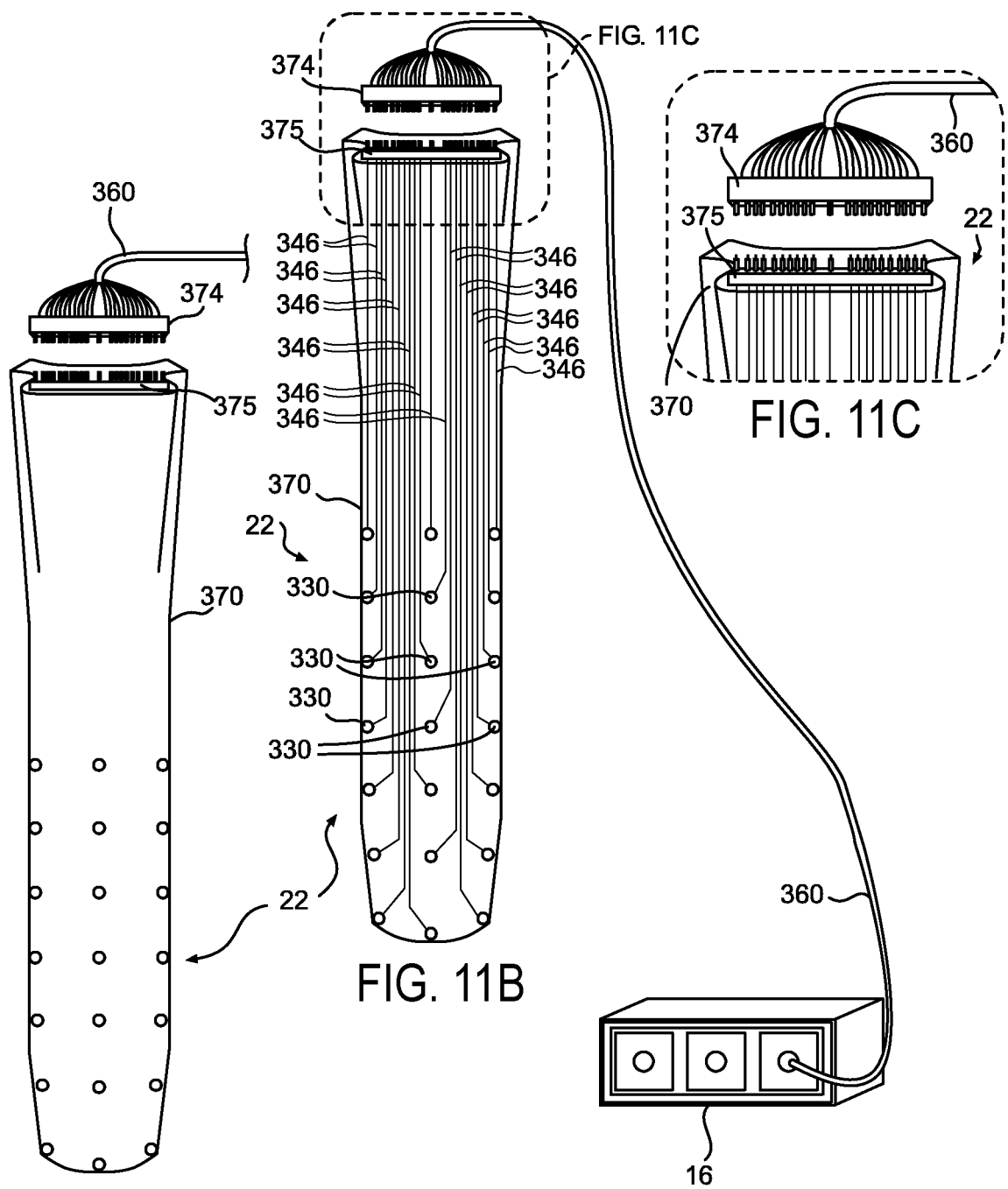
FIG. 11A depicts a front perspective view of the multi-polar grid electrode system shown in FIG. 10 according to one embodiment.
FIG. 11B depicts a cross-sectional view of the multi-polar grid electrode system shown in FIG. 11A according to one embodiment.
FIG. 11C depicts a partial magnified view of the multi-polar grid electrode system shown in FIG. 11B.
Figure 12:
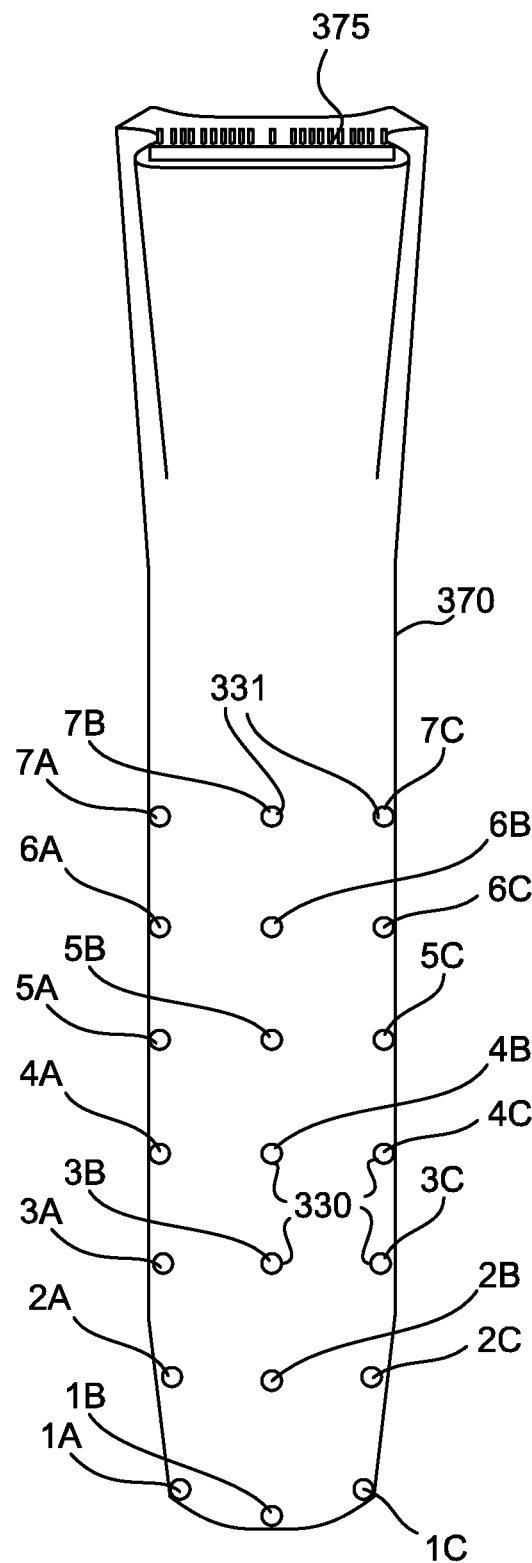
FIG. 12 depicts a front perspective view of a multi-polar grid electrode system have alphanumeric assignments according to one embodiment.

Referring to FIG. 12, The designation of alphanumeric names to each particular electrode 331 can direct the software to control the delivery of precisely controlled electrical stimulation from the multi-polar stimulation unit 16 (FIG. 11B) independently to each electrode on the grid 330 as is described in greater detail in the section on multi-polar electrical stimulation sequencing of peripheral nerves/roots with sequential motor thresholding using circumferential and planar grid arrays.

In an example planar electrode grid arrangement, the electrodes 331 can have, for example, designated names alphanumerically in a left to right and inferior to superior fashion. The planar grid can be arranged into rows and columns. In the current illustration, there are three columns (A, B & C) which can designate the horizontal position of the electrode 331 in each row which include column A (left column), column B (middle column) and column C (right column). The rows can designate the vertical position of the electrode 331 with the most distal electrodes 331 (row #1) being located in the distal end of the retractor blade 370. In the illustrated example, there are seven rows (1-7) with row #1 at the most distal tip of the retractor with subsequent numbering proceeding superiorly towards the base of the retractor. The 1A electrode can be located in the left distal end of the retractor. Each row (1-7) can have three electrodes (A, B & C) as is shown in FIG. 11A. It will be appreciated that any suitable number of electrodes having any suitable configuration or nomenclature are contemplated. The electrodes can be equally spaced apart, can have non-uniform spacing, can be concentrated in suitable areas, or can otherwise be suitably configured.

Referring to FIGS. 14A and 14B, an example embodiment of a system integrating multiple components is shown. It will be appreciated that any suitable arrangement, number, and configuration of components is contemplated.

With multi-polar sequential electrical stimulation with a grid array the size, shape, and intensity of the electrical fields can be altered by varying the current delivered to each particular electrode on the grid array. By selecting electrode configurations, currents/voltages and pulse widths, regions of the anatomy surrounding the stimulating electrodes that are electrified can be controlled. By recording evoked EMG responses from stimulation of various sets of electrodes on the grid, information can be obtained about the presence, direction, proximity and functional status of neural structures in the surgical field. Software can control the delivery of electrical current to various sets of electrodes in the grid and can simultaneously record any evoked motor EMG activity. The sets of electrodes that evoke motor responses can provide information about the presence of neural structures within the surgical field. Conversely, the absence of any evoked EMG responses (up to predetermined maximum stimulus intensity) can suggest an absence of motor neural structures within the area surrounding the stimulating electrodes. If stimulation of a particular set of electrodes on the grid evokes a motor response while other sets of electrodes do not, information can be deduced about the direction of neural structures within the surgical field in relation to the stimulating electrodes. By thresholding any evoked motor responses (calculating the minimum amount of electrical current required to elicit a motor response), information can be deduced about the proximity of the neural structures. Information about the proximity of neural structures can be based on the general understanding that neural elements in close proximity to the stimulating electrodes will elicit motor responses at a lower amount of electrical stimulus intensity (measured in milliamps) and neural elements that are relatively more distant will require a greater amount of current to elicit a motor response. A motor threshold "map" can be generated by the software and displayed after multiple sequential stimulations are delivered to various sets of electrodes on the grid.

Electrode grid design and software programming can constrain the electrical fields to control which regions of the surgical field are electrified at any given time. The stimulus timing, waveform shape and electrode polarity can create focal electrical fields for accurate motor fiber monitoring and mapping. The shape and distribution of the electrical fields created by the electrical current/voltage can be strategically controlled. The size, shape and gradient or intensity of an electrical field can be affected by the configuration of the grid electrodes and which electrodes are activated at any given time.

Multiple electrode configurations have been commonly utilized in other disciplines including cardiac pacing, FES (Functional Electrical Stimulation for muscle deprived of nervous control to providing muscular contraction and producing a functionally useful moment), DBS (Deep Brain Stimulation-implantation of electrodes for therapeutic control of movement disorders and chronic pain), SCS (Spinal Cord Stimulation—for control of chronic pain) and cochlear implants.

The software of versions herein can be designed to provide the ability to assign electrical polarity to each particular electrode on the grid. Activation of any electrode on the grid (or combinations of electrodes) with a particular assignment of polarity can result in the ability to create various combinations of shapes, sizes and spatial distributions of electrical fields. The configurability and re-configurability of the grid electrodes between successive stimulations can provide the ability to assign varied polarities and stimulation parameters to alter the generated electrical fields and thus scan the surgical field for motor evoked responses.

In addition, the software can have the ability to activate multiple electrodes in the grid simultaneously and can assign particular polarities to each of them. Activation of multiple electrodes simultaneously with varied polarities is sometimes referred to as "current steering" and can be used to increase the selectivity of a given configuration of electrodes by activating tissue that could not be activated by driving the electrodes independently.

This ability to assign polarities and stimulus parameters to one or multiple electrodes on the grid can allow the multipolar grid array system to utilize multiple stimulation paradigms to vary the size, shape and distributions of the electrical fields (mono-polar, bipolar, tripolar, etc.). The software program can be varied to deliver specific types of stimulation or sequences of stimulations according to the surgical situation and the particular monitoring/mapping requirements.

Figure 15D:
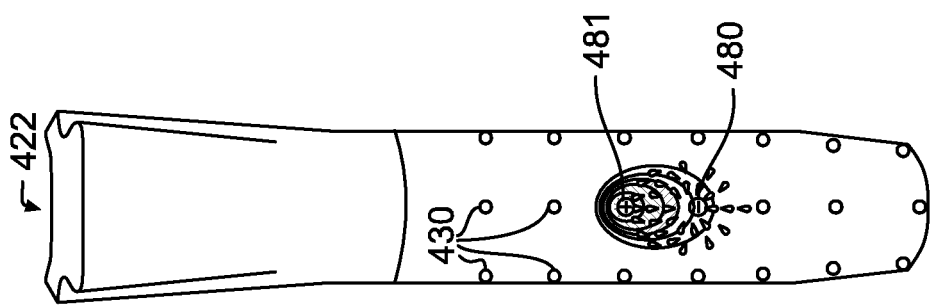
FIG. 15D depicts a front perspective view of the stimulation system of FIG. 15A, shown indicating a second bi-polar response.
Figure 15C:
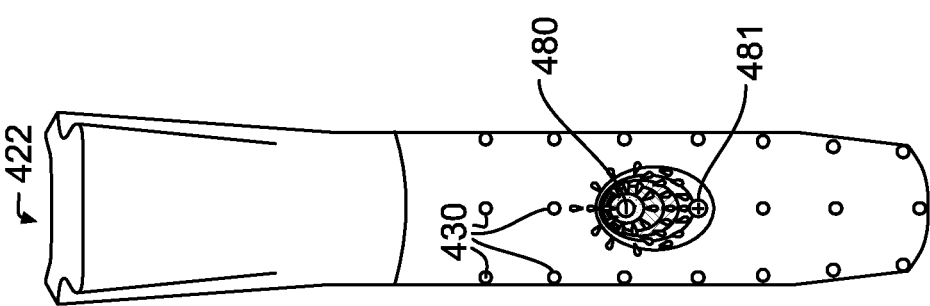
FIG. 15C depicts a front perspective view of the stimulation system of FIG. 15A, shown indicating a first bi-polar response.
Figure 15B:
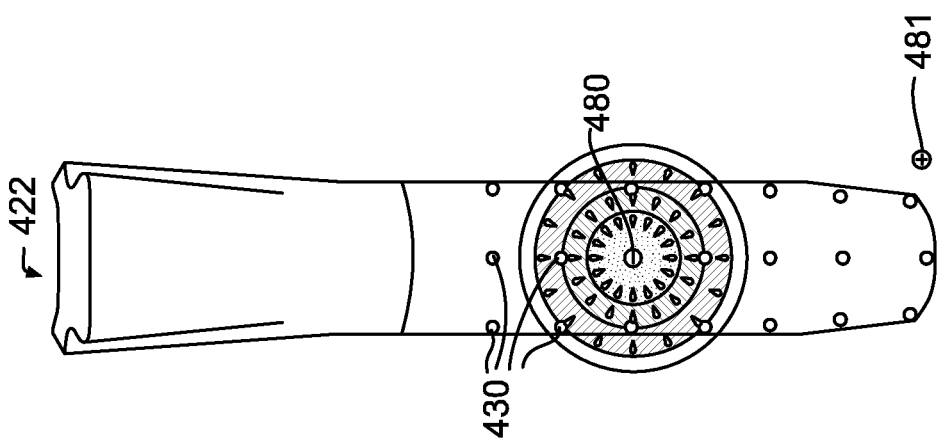
FIG. 15B depicts a front perspective view of the stimulation system of FIG. 15A, shown indicating a mono-polar response.
Figure 15A:
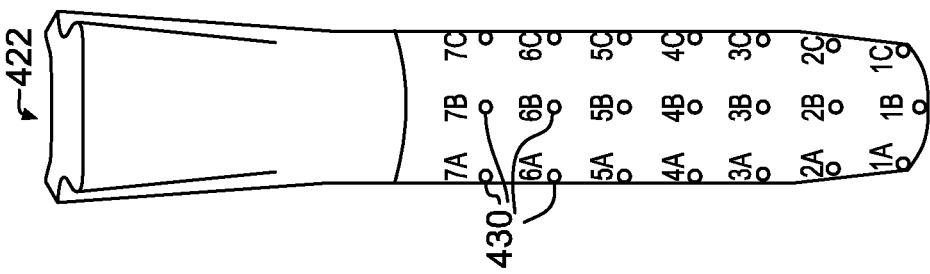
FIG. 15A depicts a front perspective view of a stimulation system according to one embodiment shown with alphanumeric electrode designations.

FIGS. 15A-17D illustrate example stimulation paradigms for multi-polar planar grid electrode arrays. FIG. 15A illustrates one version of mono-polar stimulation where the system 422 can include only a single cathode (negative) electrode 480 activated on the grid 430. In mono-polar stimulation, the return electrode or anode 481 (positive) can placed at some distance away from the cathode 480. The electrical field lines can emit radially outward from the source of the current, the cathode (−), and the return current at the anode (+) can be placed at a distant site. Mono-polar stimulation can be more useful in some particular situations when sensitivity is forever over specificity.

FIGS. 15C and 15D also illustrate examples of bipolar stimulation. In a bipolar stimulation configuration, current can travel from one electrode (a cathode 480 or negative electrode) to another peripheral electrode (an anode 481 or positive electrode). With bipolar stimulation, the electrical charge can flow from the negative cathode 480 to the positive anode 481 as shown by the electrical field lines. This results can be a more focused, localized stimulation. Bi-polar stimulation can result in less current spread than mono-polar stimulation and therefore smaller, more selective activation.

Bipolar stimulation can be delivered by designating any two electrodes on this grid as a cathode 480 and anode 481, for example. FIGS. 15C and 15D illustrate 2 two different electrical fields that can be generated with bi-polar stimulation when different electrodes are assigned as the cathode 480 and anode 481. In one example, as shown in FIG. 15C, the cathode 480 is assigned to electrode 5B while the anode 481 is assigned to electrode 4B. In FIG. 15D, the assigned polarities can be reversed with the cathode 480 assigned to electrode 4B while the anode 481 can be assigned to electrode 5B.

Figure 16A:
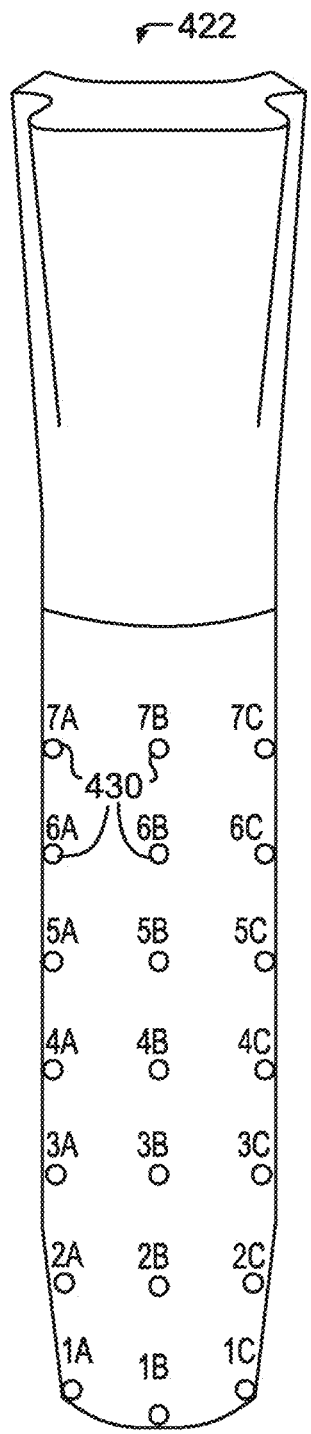
FIG. 16A depicts a front perspective view of a bi-polar stimulation system according to one embodiment shown with alphanumeric electrode designations.
Figure 16B:
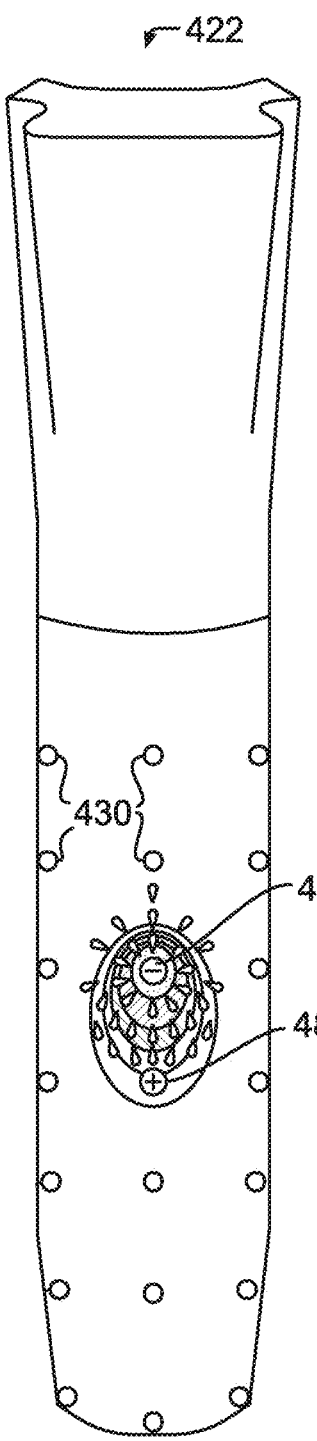
FIG. 16B depicts a front perspective view of the bi-polar stimulation system of FIG. 16A, shown indicating a first response.
Figure 16C:
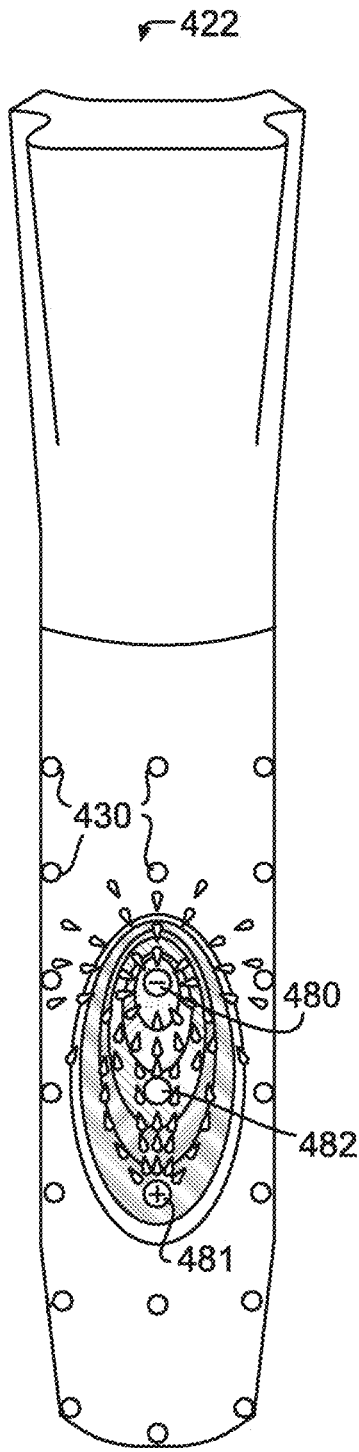
FIG. 16C depicts a front perspective view of the bi-polar stimulation system of FIG. 16A, shown indicating a second response.

FIGS. 16A-16C illustrate examples of different sub-types of bi-polar stimulation and how the distance between the two electrodes 480, 481 can have significant effects on the size, shape and orientation of the induced electrical fields. FIG. 16B represents one version of narrow bi-polar stimulation where there can be a short distance between the cathode 480 (electrode 5B) and anode 481 (electrode 4B) that can result in a localized, focal electrical field. In a wider bi-polar configuration, as illustrated in FIG. 16C, there can be a greater distance between the cathode 480 (electrode 5B) and anode 481 (3B) which can result in a larger current distribution. In this instance, there can be an inactive electrode 482 (4B) which can separate the cathode 480 (5B) and anode 481 (3B).

Figure 17A:
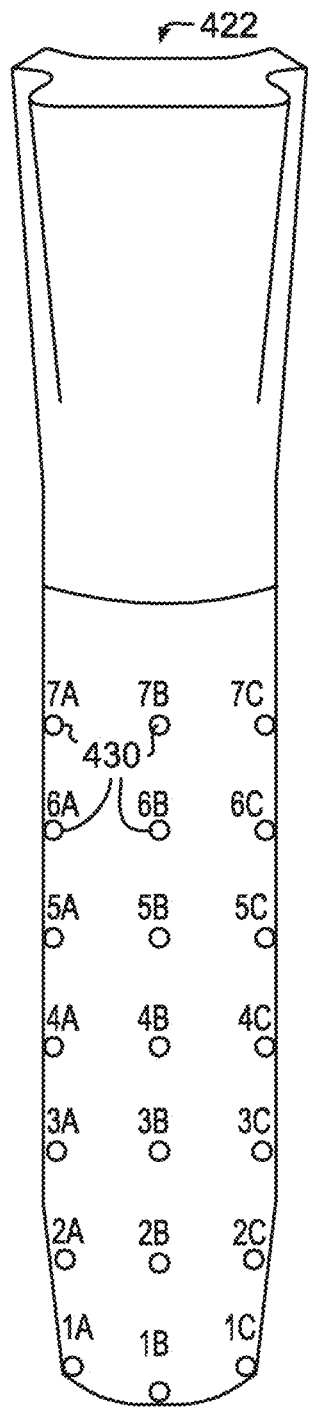
FIG. 17A depicts a front perspective view of a tri-polar stimulation system according to one embodiment shown with alphanumeric electrode designations.
Figure 17B:
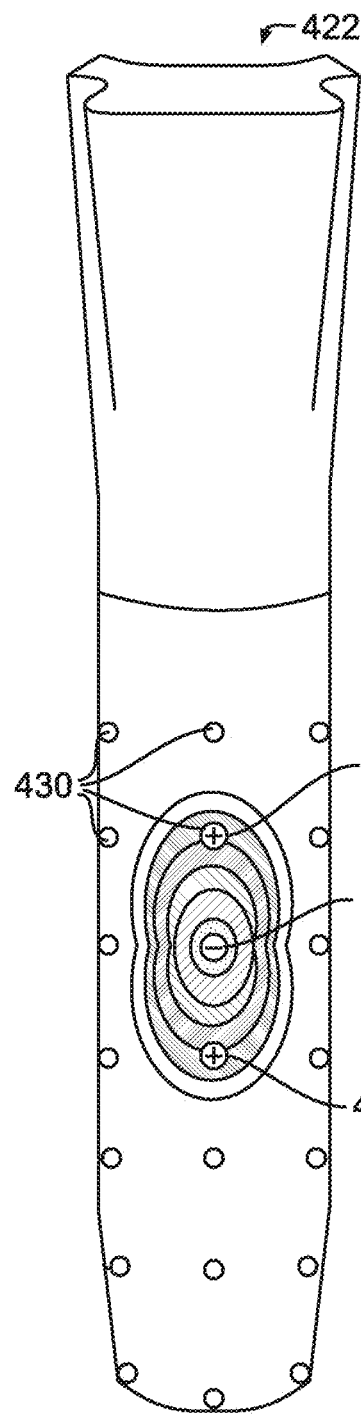
FIG. 17B depicts a front perspective view of the tri-polar stimulation system of FIG. 17A, shown indicating a first response.
Figure 17C:
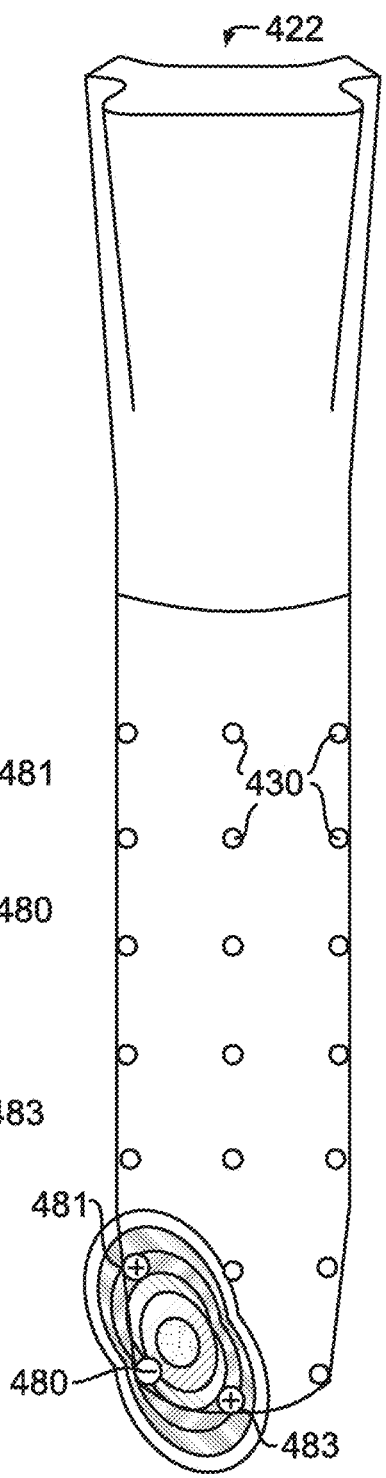
FIG. 17C depicts a front perspective view of the tri-polar stimulation system of FIG. 17A, shown indicating a second response.

FIGS. 17A-C illustrate examples of tri-polar stimulation systems 422 where a single cathode 480 can be active and can send current to a first anode 481 and a second anode 483 that can share an equal potential difference. Tri-polar stimulation may be beneficial because it can more effectively localize the electrical field and limit the amount of current spread. In the example shown in FIG. 17B, the single cathode 480 can be assigned to electrode 5B, and first and second anodes 481, 483 can be assigned in a linear arrangement above and below the cathode at 6B and 4B. In the example shown in FIG. 17C, there can be a single cathode 480 that can be assigned to electrode 1A and first and second anodes 481, 483 that can be positioned perpendicularly at 2A and 1B. The theoretical shapes of the electrical fields generated by both of these tripolar arrangements are illustrated. Other tri-polar arrangements are possible including wide tri-polar arrangements with a greater separate distance between the cathode and anodes. Many other multipolar electrode assignments can be envisioned with any combination of electrode assignments including differing numbers of active anodes and cathodes. Certain combinations of electrode assignments may be found to be useful in controlling the generated electrical fields to optimize nerve fiber localization in the surgical field. The optimal electrode assignments and sequencing of stimulations may be determined with mathematical modeling and experimental studies.

These examples of the different stimulation paradigms illustrate how various electrical fields can be created by systematically and strategically assigning different polarities and stimulation schemes to various electrodes on the grid electrode array. By combining the information gained from multiple sequences of stimulations, a threshold map of the evoked responses can be obtained, which can localize the presence of motor fibers in the surgical field in relation to the grid electrodes. Mathematical modeling and/or experimental studies may guide the software programming towards the optimal electrode polarity assignments and stimulation sequencing protocols that would map a surgical site most efficiently. An efficient stimulation sequence can then quickly generate a color coded map that can be displayed to inform the surgeon of the location and proximity of neural structures located within the surgical field. Examples described herein can utilize these unique systems and methods to improve the accuracy and resolution of nerve mapping and can increase the surface area along the depth of the operative corridor which can be mapped and monitored compared to existing materials and methods of nerve monitoring and mapping.

In general, it will be apparent to one of ordinary skill in the art that at least some of the embodiments described herein can be implemented in many different embodiments of software, firmware, and/or hardware. The software and firmware code can be executed by a processor or any other similar computing device. The software code or specialized control hardware that can be used to implement embodiments is not limiting. For example, embodiments described herein can be implemented in computer software using any suitable computer software language type, using, for example, conventional or object-oriented techniques. Such software can be stored on any type of suitable computer-readable medium or media, such as, for example, a magnetic or optical storage medium. The operation and behavior of the embodiments can be described without specific reference to specific software code or specialized hardware components. The absence of such specific references is feasible, because it is clearly understood that artisans of ordinary skill would be able to design software and control hardware to implement the embodiments based on the present description with no more than reasonable effort and without undue experimentation.

Moreover, the processes described herein can be executed by programmable equipment, such as computers or computer systems and/or processors. Software that can cause programmable equipment to execute processes can be stored in any storage device, such as, for example, a computer system (nonvolatile) memory, an optical disk, magnetic tape, or magnetic disk. Furthermore, at least some of the processes can be programmed when the computer system is manufactured or stored on various types of computer-readable media.

It can also be appreciated that certain portions of the processes described herein can be performed using instructions stored on a computer-readable medium or media that direct a computer system to perform the process steps. A computer-readable medium can include, for example, memory devices such as diskettes, compact discs (CDs), digital versatile discs (DVDs), optical disk drives, or hard disk drives. A computer-readable medium can also include memory storage that is physical, virtual, permanent, temporary, semi-permanent, and/or semi-temporary.

A "computer," "computer system," "host," "server," or "processor" can be, for example and without limitation, a processors, microcomputer, minicomputer, server, mainframe, laptop, personal data assistant (PDA), wireless e-mail device, cellular phone, pager, processors, fax machine, scanner, or any other programmable device configured to transmit and/or receive data over a network. Computer systems and computer-based devices disclosed herein can include memory for storing certain software modules used in obtaining, processing, and communicating information. It can be appreciated that such memory can be internal or external with respect to operation of the disclosed embodiments. The memory can also include any means for storing software, including a hard disk, an optical disk, floppy disk, ROM (read only memory), RAM (random access memory), PROM (programmable ROM), EEPROM (electrically erasable PROM) and/or other computer-readable media. Non-transitory computer-readable media, as used herein, comprises all computer-readable media except for a transitory, propagating signals.

In various embodiments disclosed herein, a single component can be replaced by multiple components and multiple components can be replaced by a single component to perform a given function or functions. Except where such substitution would not be operative, such substitution is within the intended scope of the embodiments. The computer systems can comprise one or more processors in communication with memory (e.g., RAM or ROM) via one or more data buses. The data buses can carry electrical signals between the processor(s) and the memory. The processor and the memory can comprise electrical circuits that conduct electrical current. Charge states of various components of the circuits, such as solid state transistors of the processor(s) and/or memory circuit(s), can change during operation of the circuits.

Some of the figures can include a flow diagram. Although such figures can include a particular logic flow, it can be appreciated that the logic flow merely provides an exemplary implementation of the general functionality. Further, the logic flow does not necessarily have to be executed in the order presented unless otherwise indicated. In addition, the logic flow can be implemented by a hardware element, a software element executed by a computer, a firmware element embedded in hardware, or any combination thereof.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. A nerve mapping system comprising:
a computer system configured to:
cause delivery of sequential variable multi-polar stimulation to electrodes of a grid array of electrodes according to a plurality of stimulation configurations to scan the grid array and elicit evoked potential responses, wherein the plurality of stimulation configurations include at least mono-polar, bi-polar, and tri-polar stimulation configurations of different electrodes of the grid array, and wherein the electrodes are positioned on a surface of an instrument configured to be inserted into a tissue site of a patient to map locations and proximities of neural structures in the tissue site; and
receive the evoked potential responses and combine information gathered based on the evoked potential responses to enable nerve mapping.

2. The nerve mapping system of claim 1, wherein each of the electrodes is configured to be stimulated individually and independently, and wherein every one of the electrodes is configured to be stimulated as part of at least mono-polar, bi-polar, and tri-polar stimulation configurations.

3. The nerve mapping system of claim 1, wherein the computer system is further configured to:
generate a virtual map of locations and proximities of neural structures in the tissue site based at least in part on the information gathered based on the evoked potential responses.

4. The nerve mapping system of claim 3, wherein the virtual map includes:
a graphical representation of the instrument including a graphical representation of the grid array and positions of the electrodes of the grid array overlaid on the graphical representation of the instrument; and
one or more colors overlaid on the graphical representation of the instrument including the graphical representation of the grid array of electrodes, wherein the one or more colors indicate the locations and proximities of the neural structures in relation to the instrument and to each electrode of the grid array of electrodes on the surface of the instrument.

5. The nerve mapping system of claim 3, wherein the computer system is further configured to:
output the virtual map for display on an electronic display.

6. The nerve mapping system of claim 1, wherein the instrument comprises at least one of: a probe, a tissue dilator, or a retractor system.

7. The nerve mapping system of claim 1, wherein the instrument comprises a probe for peripheral nerve mapping.

8. The nerve mapping system of claim 1, wherein the instrument comprises a combination of a retractor system, a plurality of tissue dilators, and a probe, and wherein each of the retractor system, the plurality of tissue dilators, and the probe includes at least a portion of the grid array of electrodes.

9. The nerve mapping system of claim 1, wherein the computer system is further configured to:
adjust one or more stimulation parameters when causing delivery of stimulation to electrodes of the grid array, wherein the one or more stimulation parameters include at least one of: current level, voltage level, or pulse width.

10. An apparatus for nerve mapping, the apparatus comprising:
an instrument configured to be inserted into a tissue site of a patient; and
a grid array of a plurality of electrodes positioned on a surface of the instrument and configured to enable mapping of locations and proximities of neural structures in the tissue site, wherein:
each of the plurality of electrodes is configured to be stimulated individually and independently according to a plurality of stimulation configurations to scan the grid array and elicit evoked potential responses, and
every one of the plurality of electrodes is configured to be stimulated as part of at least mono-polar, bi-polar, and tri-polar stimulation configurations of different electrodes of the grid array.

11. The apparatus of claim 10, wherein the plurality of stimulation configurations involve delivery of sequential variable multi-polar stimulation to electrodes of the grid array.

12. The apparatus of claim 10, wherein the instrument comprises at least one of: a surgical probe, a tissue dilator, or a retractor system.

13. The apparatus of claim 10, wherein the instrument comprises a probe for peripheral nerve mapping.

14. The apparatus of claim 10, wherein the instrument comprises a combination of a retractor system, a plurality of tissue dilators, and a surgical probe, and wherein each of the retractor system, the plurality of tissue dilators, and the surgical probe includes at least a portion of the grid array.

15. The apparatus of claim 10, wherein the grid array comprises and arrangement of the plurality of electrodes on the surface of the instrument in a plurality of rows and a plurality of columns.

16. The apparatus of claim 10 further comprising:
one or more recording electrodes or needles configured to detect evoked potential responses elicited by stimulation of combinations of electrodes of the plurality of electrodes of the grid array according to the plurality of stimulation configurations.

17. A method of nerve mapping, the method comprising:
providing an apparatus for nerve mapping according to claim 10;
inserting the instrument, including the grid array, into a tissue site of a patient; and
initiating delivery of sequential variable multi-polar stimulation to electrodes of the plurality of electrodes of the grid array according to a plurality of stimulation configurations to scan the grid array and elicit evoked potential responses to provide nerve mapping.

18. The method of claim 17 further comprising:
causing display of a virtual map of locations and proximities of neural structures in the tissue site, wherein is virtual map is generated based at least in part on information gathered based on the evoked potential responses.

19. The method of claim 18, wherein the virtual map includes:
a graphical representation of the instrument including a graphical representation of the grid array and positions of the plurality of electrodes of the grid array overlaid on the graphical representation of the instrument; and
one or more colors overlaid on the graphical representation of the instrument including the graphical representation of the grid array, wherein the one or more colors indicate the locations and proximities of the neural structures in relation to the instrument and to each electrode of the plurality of electrodes of the grid array on the surface of the instrument.

20. The method of claim 17, wherein the instrument comprises at least one of:
- a probe for peripheral nerve mapping,
- a tissue dilator,
- a retractor system, or
- a combination of a retractor system, a plurality of tissue dilators, and a probe, and wherein each of the retractor system, the plurality of tissue dilators, and the probe of the combination includes at least a portion of the grid array.

* * * * *